[12] United States Patent
Dewey et al.

(10) Patent No.: US 10,137,007 B2
(45) Date of Patent: *Nov. 27, 2018

(54) GEARED CAM EXPANDABLE INTERBODY IMPLANT AND METHOD OF IMPLANTING SAME

(71) Applicant: Warsaw Orthopedic, Inc, Warsaw, IN (US)

(72) Inventors: Jonathan Dewey, Memphis, TN (US); William D. Armstrong, Memphis, TN (US); Anthony J. Melkent, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 174 days.

This patent is subject to a terminal disclaimer.

(21) Appl. No.: 15/147,668

(22) Filed: May 5, 2016

(65) Prior Publication Data

US 2017/0319352 A1 Nov. 9, 2017

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4425* (2013.01); *A61F 2/4611* (2013.01); *A61F 2002/30261* (2013.01); *A61F 2002/30523* (2013.01); *A61F 2002/30556* (2013.01); *A61F 2002/30579* (2013.01); *A61F 2002/30904* (2013.01); *A61F 2002/4475* (2013.01); *A61F 2250/0009* (2013.01)

(58) Field of Classification Search
CPC ....... A61F 2/4455–2/447; A61F 2/4611; A61F 2002/4475
See application file for complete search history.

(56) References Cited

U.S. PATENT DOCUMENTS

| 6,447,546 | B1 * | 9/2002 | Bramlet ................. A61F 2/446 623/17.11 |
| 6,527,803 | B1 * | 3/2003 | Crozet .................... A61F 2/442 606/31 |
| 9,801,640 | B2 * | 10/2017 | O'Neil ............... A61B 17/1671 |

(Continued)

FOREIGN PATENT DOCUMENTS

DE 29806833 U1 * 6/1998 ........... A61F 2/4455

OTHER PUBLICATIONS

English translation of the description of DE 29806833.*

*Primary Examiner* — Matthew Lawson
*Assistant Examiner* — Amy Sipp

(57) ABSTRACT

A geared cam expandable spinal implant. Rotational motion of a rotating portion is translated into linear motion of a yoke, which moves geared cams at the distal end of the implant to mate with, and walk along, teeth of corresponding racks. The walking of the gear cam teeth along the rack teeth creates a regular rate of implant expansion, reduces initial excessive expansion force applied to the implant, and provides fine adjustment of the expansion rate and force. Spikes, pivotally mounted on the yoke, pivot outward as the implant expands, to a fully-deployed position into engagement with surfaces of adjacent vertebral bodies. The engagement between the deployed spikes and the vertebral bodies prevents inadvertent backout of the expanded implant.

17 Claims, 37 Drawing Sheets

(56) References Cited

U.S. PATENT DOCUMENTS

| | | | |
|---|---|---|---|
| 2003/0236520 A1* | 12/2003 | Lim | A61B 17/025 606/99 |
| 2009/0265007 A1* | 10/2009 | Colleran | A61F 2/4465 623/17.16 |
| 2010/0137989 A1* | 6/2010 | Armstrong | A61F 2/4465 623/17.16 |
| 2010/0185289 A1* | 7/2010 | Kirwan | A61F 2/4455 623/17.11 |
| 2011/0093074 A1* | 4/2011 | Glerum | A61F 2/447 623/17.16 |
| 2013/0079883 A1* | 3/2013 | Butler | A61F 2/4425 623/17.16 |
| 2013/0158664 A1* | 6/2013 | Palmatier | A61F 2/447 623/17.16 |
| 2013/0197642 A1* | 8/2013 | Ernst | A61F 2/442 623/17.16 |
| 2013/0245767 A1* | 9/2013 | Lee | A61F 2/447 623/17.16 |
| 2014/0194991 A1* | 7/2014 | Jimenez | A61F 2/442 623/17.15 |
| 2014/0336764 A1* | 11/2014 | Masson | A61F 2/446 623/17.15 |
| 2014/0343678 A1* | 11/2014 | Suddaby | A61F 2/46 623/17.16 |
| 2015/0272743 A1* | 10/2015 | Jimenez | A61F 2/447 623/17.16 |
| 2016/0166396 A1* | 6/2016 | McClintock | A61F 2/30771 623/17.16 |
| 2016/0331542 A1* | 11/2016 | Faulhaber | A61F 2/447 |
| 2017/0128226 A1* | 5/2017 | Faulhaber | A61F 2/30767 |

\* cited by examiner

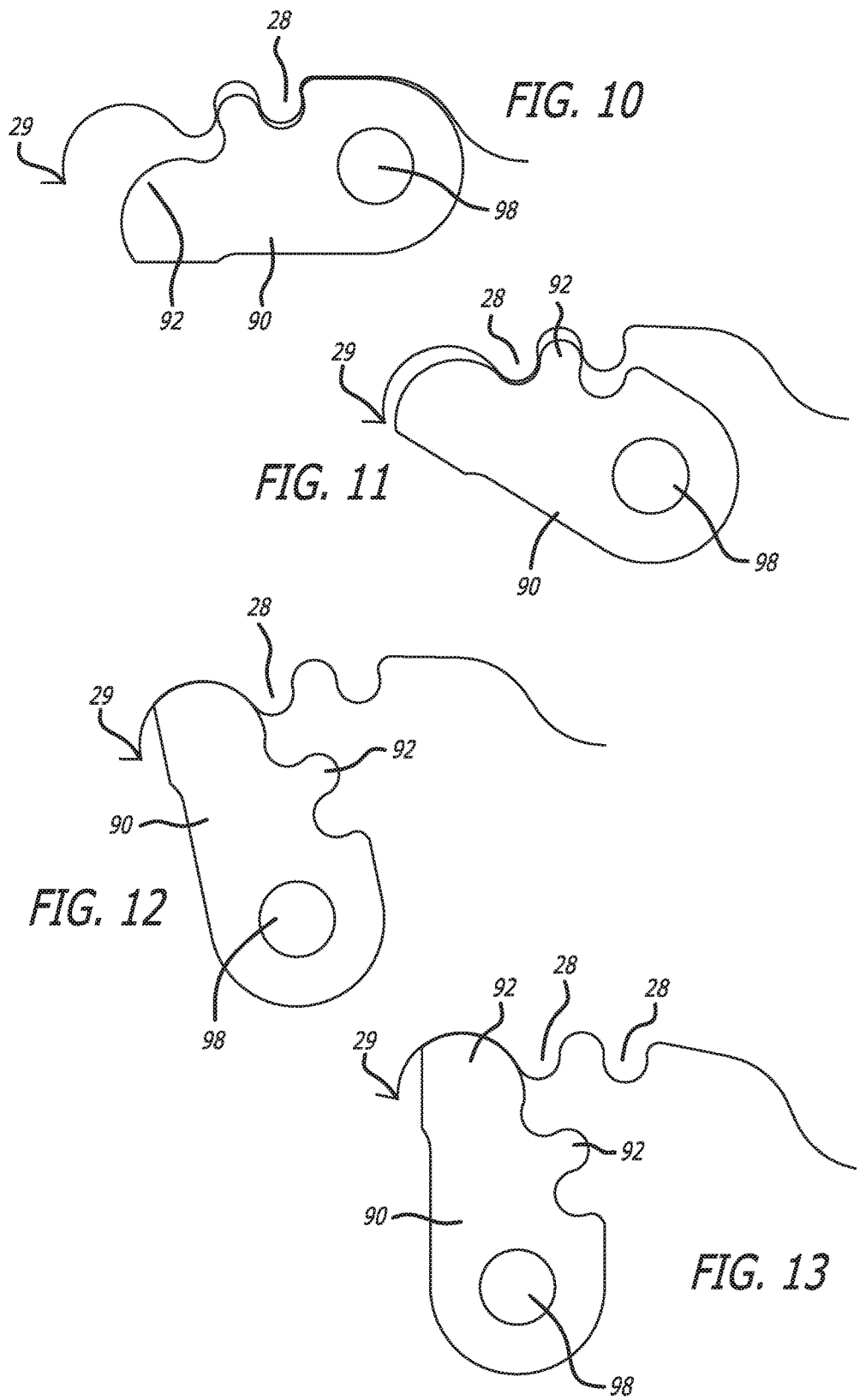

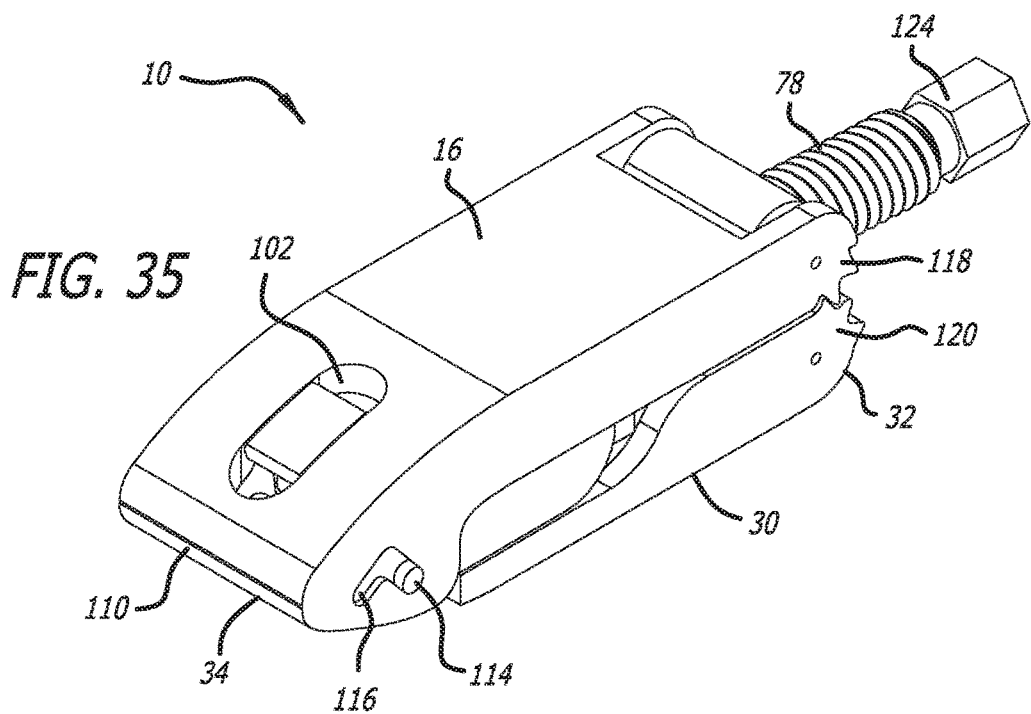
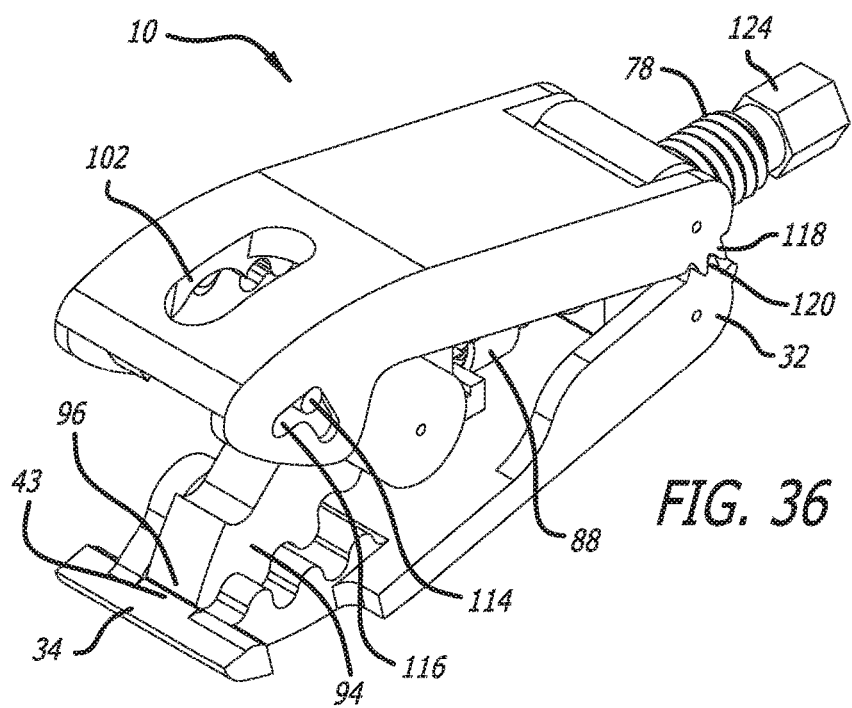

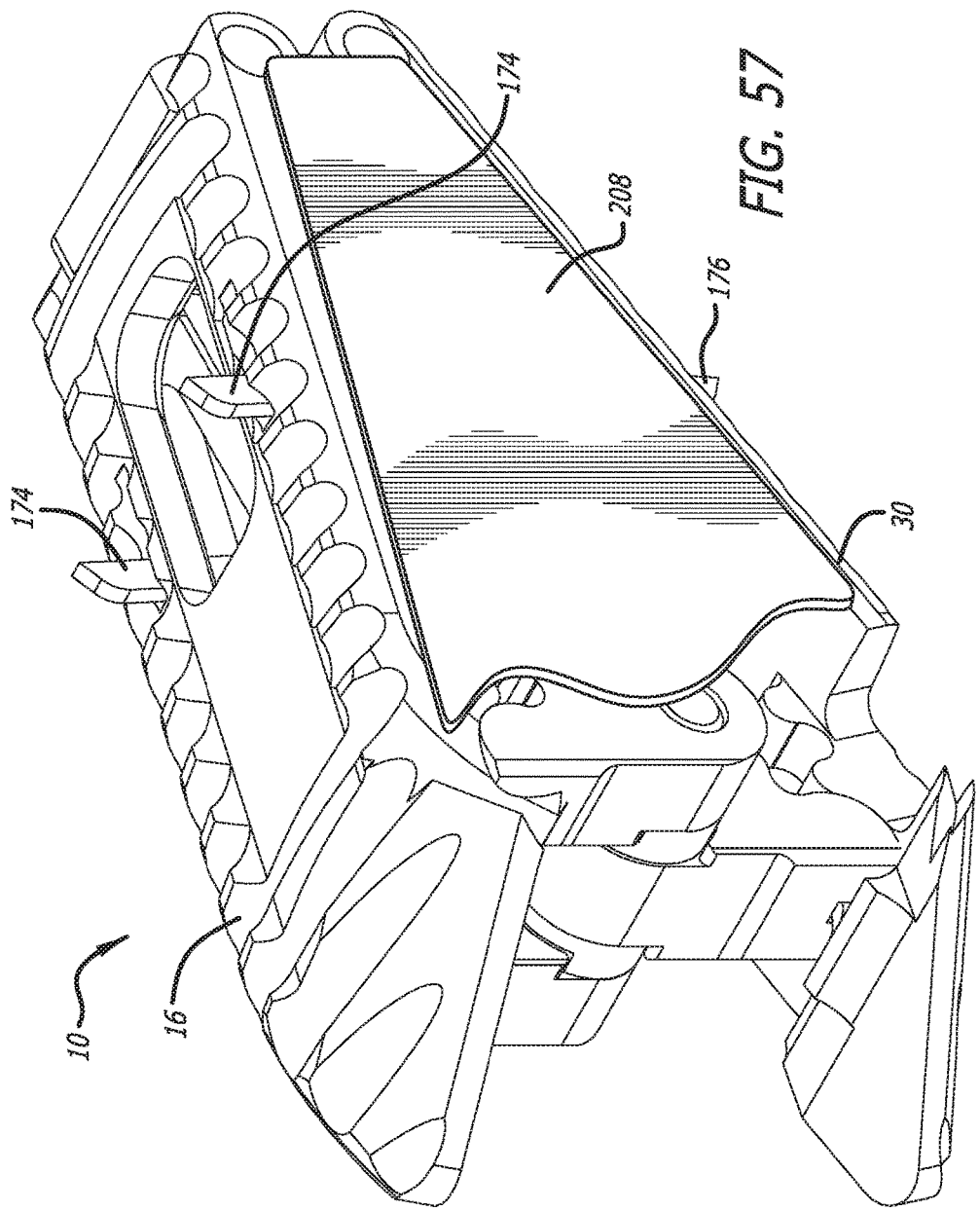

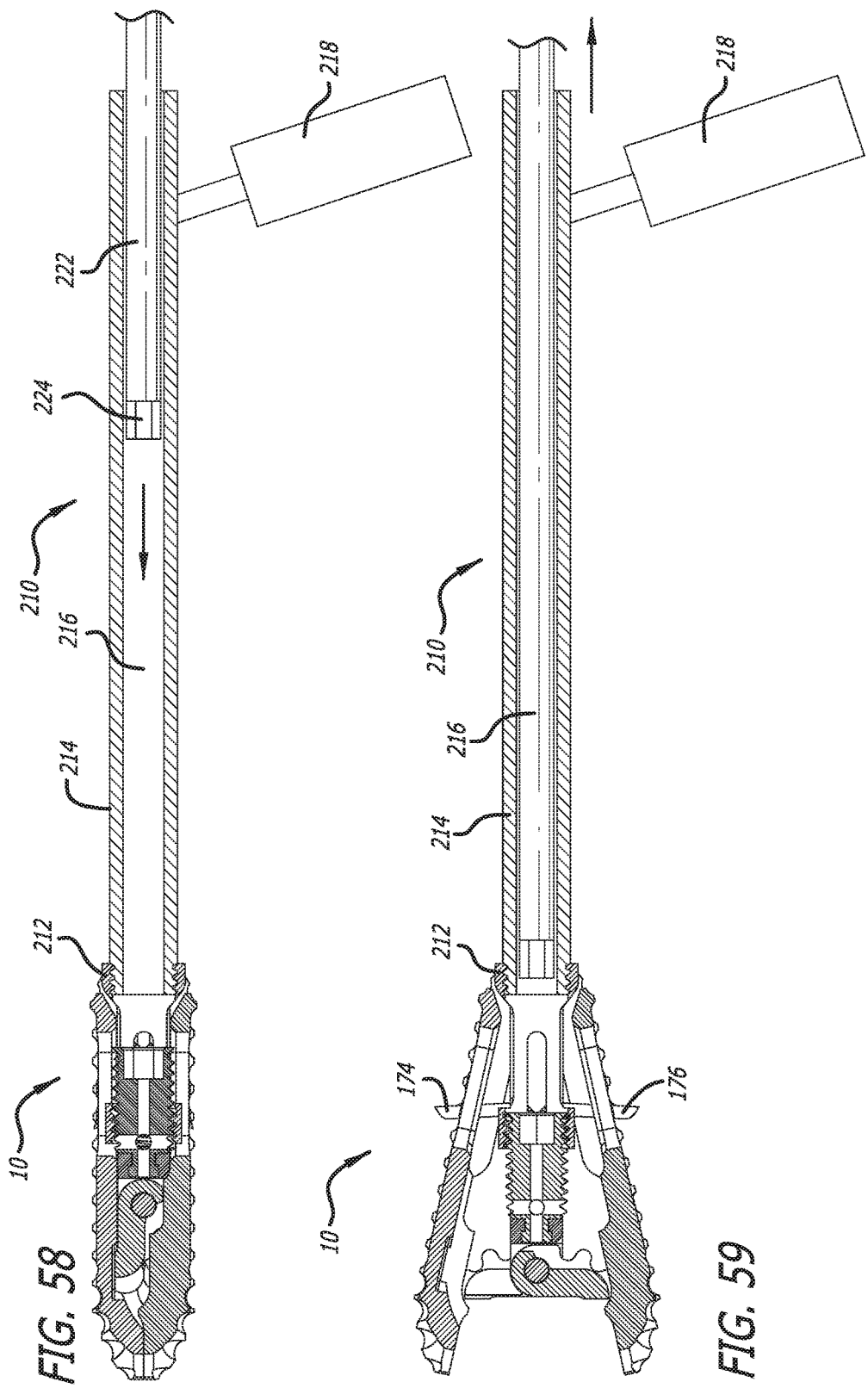

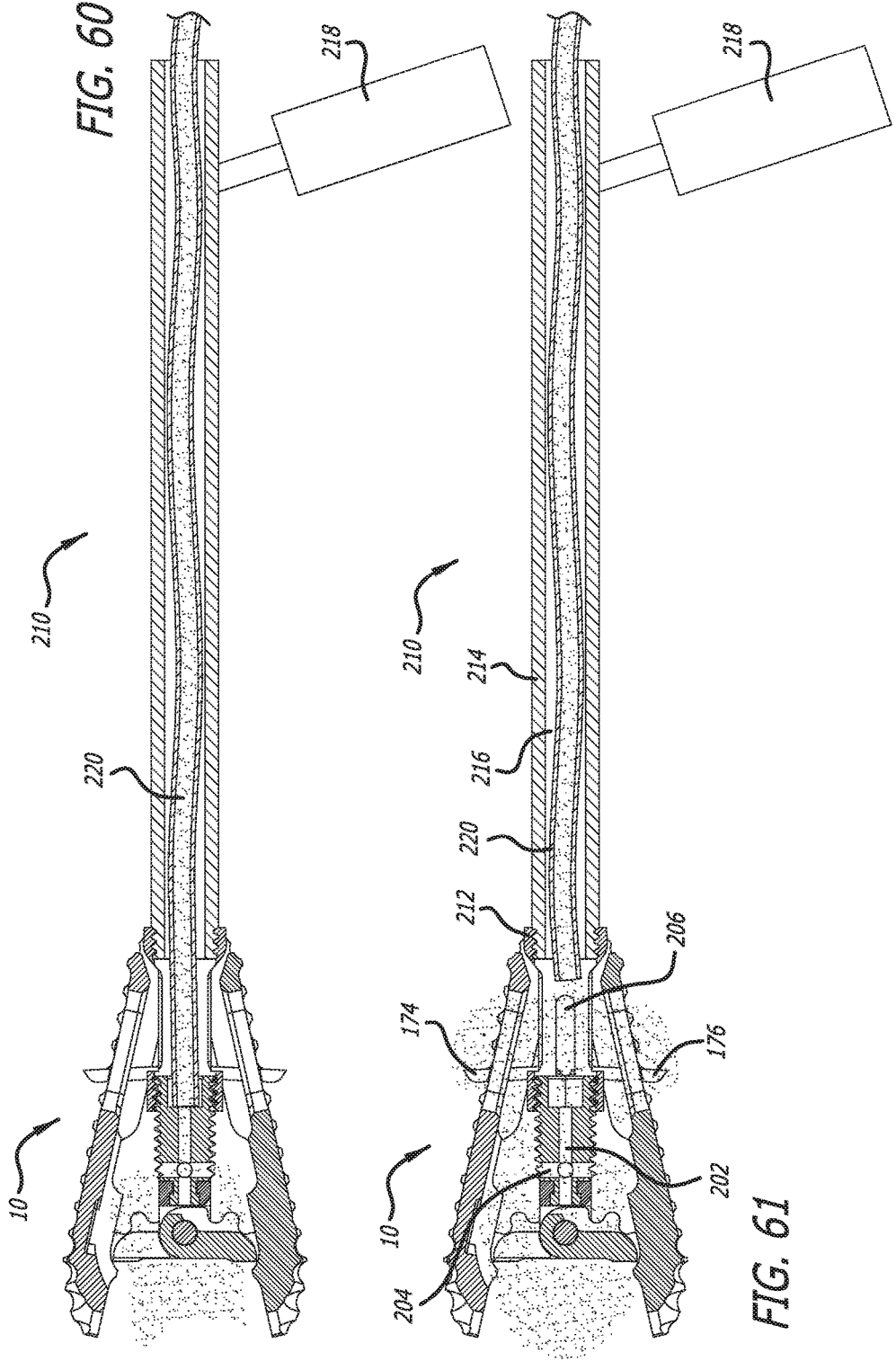

GEARED CAM EXPANDABLE INTERBODY IMPLANT AND METHOD OF IMPLANTING SAME

FIELD OF THE INVENTION

The present invention relates to a spinal implant, and a method for implanting the implant in a patient's disc space between two adjacent vertebral bodies. More particularly, the present invention relates to an expandable spinal implant including geared cams, configured to expand within the patient's disc space, from a collapsed position to an expanded position.

DESCRIPTION OF THE RELATED ART

Expandable spinal implants are known. Existing expandable spinal implants use conventional "4-bar" and "crank slider" expansion mechanisms. Following insertion, while in the collapsed position, into a surgically-enhanced disc space, the existing expandable spinal implants are expanded. The existing expandable implants have been known at least to (1) apply an undesirable excessive initial expansion force to the disc space, (2) apply an irregular expansion force to the disc space, (3) occasionally inadvertently back out of the disc space, and (4) lack a reliable capability for fine adjustment. Existing expandable implants also lack different configurations at the distal tip of the implant, which often could be advantageous, e.g., to ensure engagement between the distal tip and the adjacent vertebral bodies.

SUMMARY OF THE INVENTION

It is an object of the present invention to provide an expandable spinal implant which obviates one or more of the shortcomings of the related art.

It is another object of the present invention to provide an expandable spinal implant for insertion into a patient's disc space between an upper vertebral body and a lower vertebral body. The implant has a proximal end and a distal end defining a mid-longitudinal axis therebetween, and is expandable between a collapsed position, a partially-expanded position, and a fully-expanded position.

The implant includes an upper endplate. The upper endplate has a proximal end, a distal end, an outer surface, first and second side surfaces, and an inner surface. A portion of the inner surface includes an upper rack portion. The upper rack portion includes downwardly-projecting teeth intermediate the proximal end and the distal end of the upper endplate, and at least one distal-most downwardly-projecting tooth proximate the distal end of the upper endplate. The implant further includes a lower endplate. The lower endplate has a proximal end, a distal end, an outer surface, first and second side surfaces, and an inner surface. A portion of the inner surface includes a lower rack portion. The lower rack portion includes upwardly-projecting teeth intermediate the proximal end and the distal end of the lower endplate, and at least one distal-most upwardly-projecting tooth proximate the distal end of the lower endplate. The proximal end of the lower endplate is pivotally connected to the proximal end of the upper endplate.

A chassis portion is mounted within the implant between the upper endplate and the lower endplate. The chassis portion has a proximal end and a distal end. The proximal end has an opening defined therein.

A yoke is movably mounted within the chassis portion. The yoke has a proximal end and a distal end. The yoke is defined by first and second parallel spaced-apart walls extending from the proximal end to the distal end. A distal cross-piece, transverse to the longitudinal axis, connects the distal ends of the first and second walls of the yoke.

A rotating portion is rotatably mounted within the chassis portion. The rotating portion has a proximal end and a distal end. The distal end is configured to contact the distal cross-piece of the yoke. The proximal end has an opening defined therein, configured to receive a distal end of an implant expansion tool.

At least one first spur gear is rotatably mounted on a distal end of one of the first and second walls of the yoke. The at least one first spur gear has teeth configured to engage the downwardly-projecting teeth of the upper rack portion. At least one second spur gear is rotatably mounted on a distal end of one of the first and second walls of the yoke. The at least one second spur gear has teeth configured to engage the upwardly-projecting teeth of the lower rack portion.

The rotating portion is configured to translate rotational motion thereof to linear motion of the yoke. The yoke translates the linear motion to rotation of the spur gears with respect to the yoke, causing the spur gears to walk along the upper rack gear teeth and lower rack gear teeth, respectively, toward the distal end of the implant, thereby moving the implant through the partially-expanded position. When the spur gear teeth abut against the distal-most teeth, respectively of the upper rack or the lower rack, the implant has reached the fully-expanded position.

One or more spikes are pivotally mounted in pockets within the implant. The linear motion of the yoke pushes distal ends of the spikes into contact with ramped surfaces defined in openings in the upper and lower endplates. Contact with the ramped surfaces causes the one or more spikes to pivot to fully-deployed positions, with distal edges of the one or more spikes engaging the upper and lower vertebral bodies. This engagement between the distal edges of the one or more spikes, and the upper and lower vertebral bodies prevents the implant, in the fully-expanded position, from inadvertently backing out of the disc space.

First and second flaps are attached to the respective first and second side surfaces of the upper endplate and the lower endplate. The flaps can be made of porous, semi-porous, or solid materials, depending on the application. When the implant is in the collapsed position, the flaps can either be stretched tight between the respective side surfaces, or hang loosely between the respective side surfaces. When the implant is fully expanded, the flaps are stretched tight between the respective side surfaces, functioning as a barrier to prevent bone graft material from leaking out of the sides of the fully expanded implant.

It is a further object of the present invention to provide a method of implanting the expandable spinal implant described above into a patient's disc space between an upper vertebral body and a lower vertebral body. The method includes inserting the implant into a surgically-prepared disc space, in the collapsed position, using an implant insertion tool, rotating the rotating portion, defining a rotational motion, translating the rotational motion of the rotating portion into a linear motion of the yoke toward the distal end of the implant, rotating the spur gears with respect to the yoke, thereby walking the spur gears along the projecting teeth of the respective upper and lower racks, and expanding the implant through the partially-expanded position to the fully-expanded position. The linear motion of the yoke also translates into pivotal motion of the one or more spikes mounted in the implant. The one or more spikes pivot from a collapsed position in the implant to a fully-deployed position with distal ends in engagement with upper and lower vertebral bodies adjacent the disc space. The fully-deployed spikes, in engagement with the upper and lower vertebral bodies, prevent the fully-expanded implant from backing out of the disc space. The insertion tool includes an outer hollow shaft, an inner hollow shaft configured to pass through the outer shaft, and an elongated driver configured to pass through the inner hollow shaft. The elongated driver has a blunt distal end configured to contact a portion of the implant. Application of a movement to the elongated driver is transferred to the implant, forcing the implant into the disc space. After removal of the elongated driver, bone growth material can be routed through the inner shaft and into the implant. The one or more fully-deployed spikes, in engagement with the upper and lower vertebral bodies, prevent the fully-expanded implant from inadvertently backing out of the disc space.

These and other objects of the present invention will be apparent from review of the following specification and the accompanying drawings.

BRIEF DESCRIPTION OF THE DRAWINGS

FIGS. 10-16 are side schematic views of a multi-stage expansion mechanism used in one preferred embodiment of a geared cam expandable spinal implant in accordance with the invention;

FIG. 35 is an upper perspective view of a geared cam expandable spinal implant in accordance with the invention in a collapsed position;

FIG. 36 is an upper perspective view of a geared cam expandable spinal implant in accordance with the invention in a fully expanded position;

FIG. 57 is a front view of a geared cam expandable implant in accordance with the invention, including flaps attached to sides of the implant, in a closed position;

FIG. 58 is an upper view of a geared cam expandable implant in accordance with the invention, including flaps attached to sides of the implant, in a closed position;

FIG. 59 is a side view of a geared cam expandable implant in accordance with the invention, including flaps attached to sides of the implant, in a closed position;

FIG. 60 is a side cross-sectional view of a geared cam expandable implant in accordance with the invention, in a collapsed position, with a bone graft insertion apparatus connected to a proximal end of the implant;

FIG. 61 is a side cross-sectional view of a geared cam expandable implant in accordance with the invention, in a fully expanded position, with a bone graft insertion apparatus connected to a proximal end of the implant.

DETAILED DESCRIPTION OF THE PREFERRED EMBODIMENTS

A geared cam expandable spinal implant 10 is configured to be inserted in a surgically-enhanced disc space between an upper vertebral body and an adjacent lower vertebral body. The implant 10 includes a proximal end 12 and a distal end 14, defining a mid-longitudinal axis L-L therebetween.

Figure 6:
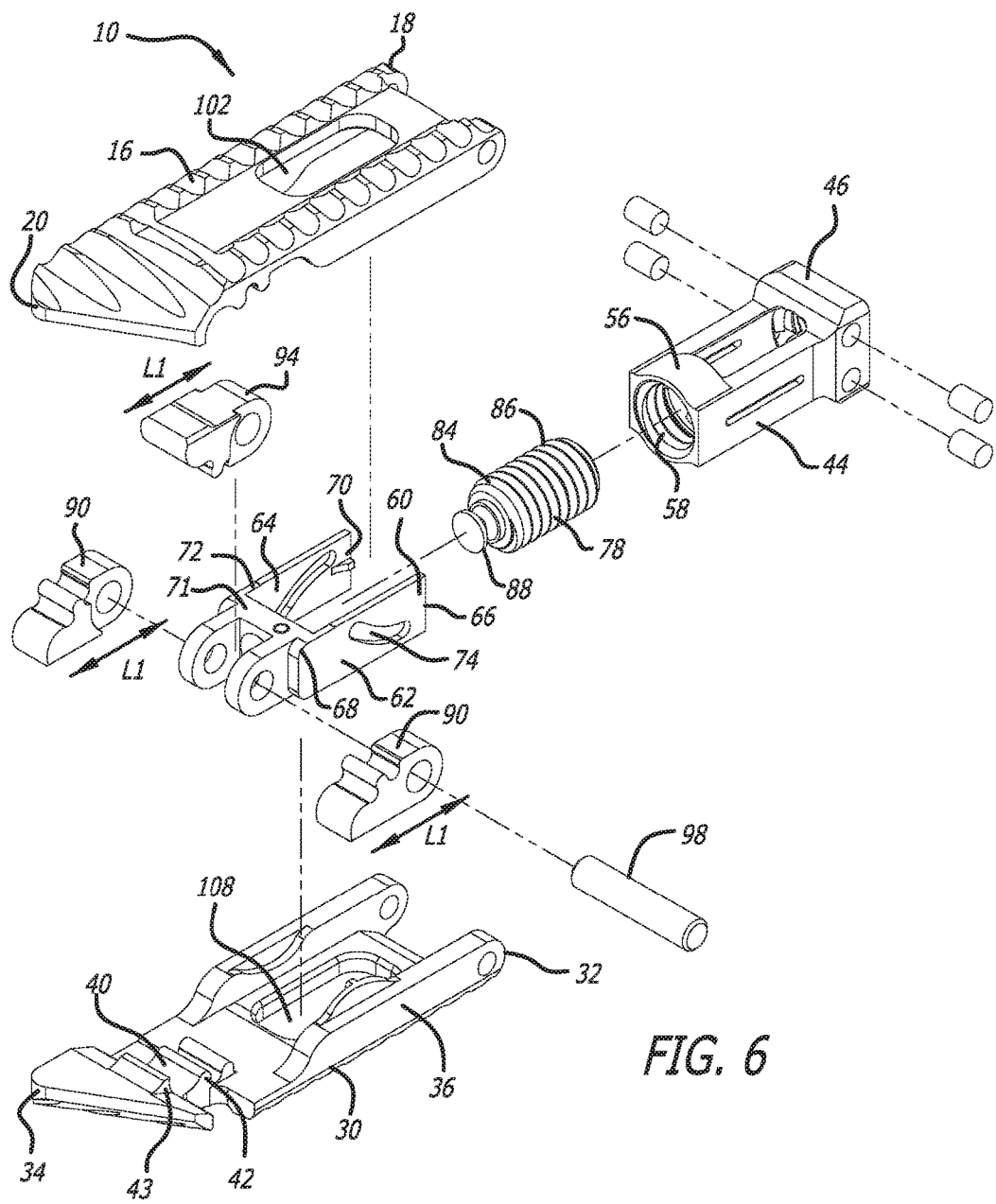
FIG. 6 is an exploded parts view of a geared cam expandable spinal implant in accordance with the invention.
Figure 7:
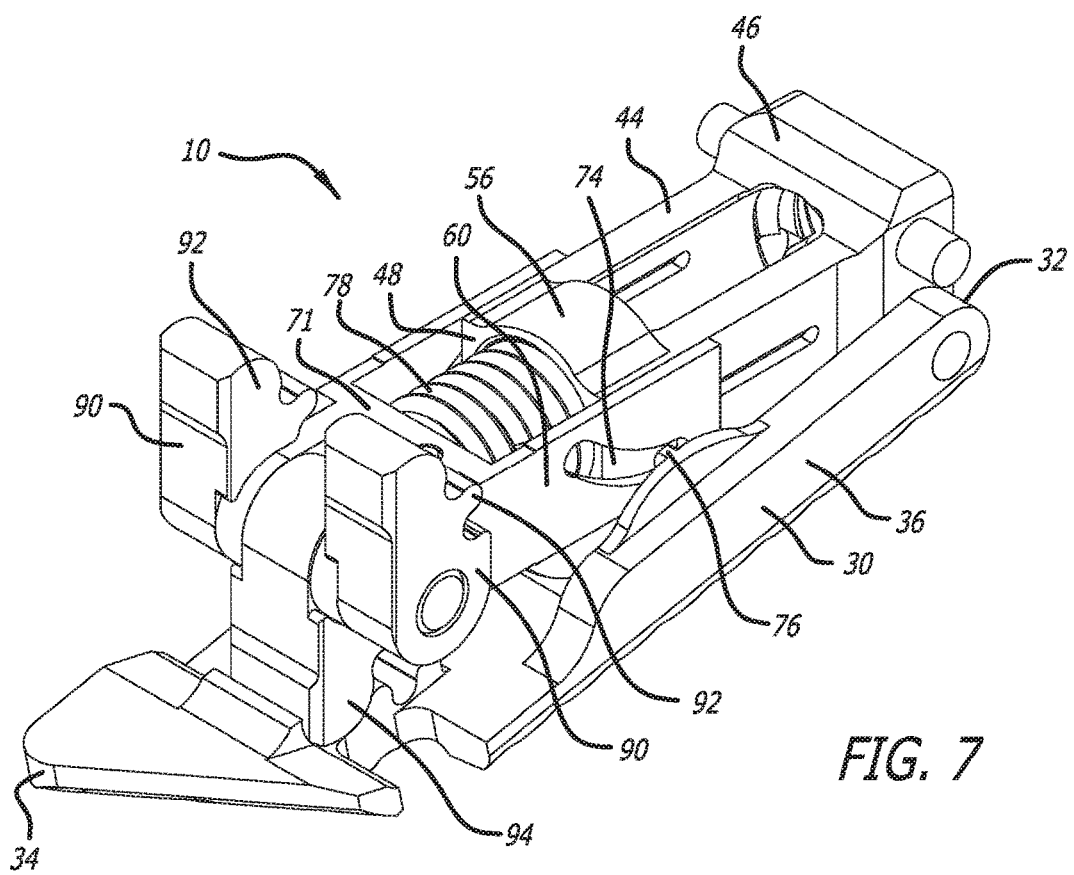
FIG. 7 is an upper perspective view of a lower endplate, chassis portion, yoke, rotating portion, and spur gears, of a geared cam expandable spinal implant in accordance with the invention.
Figure 8:
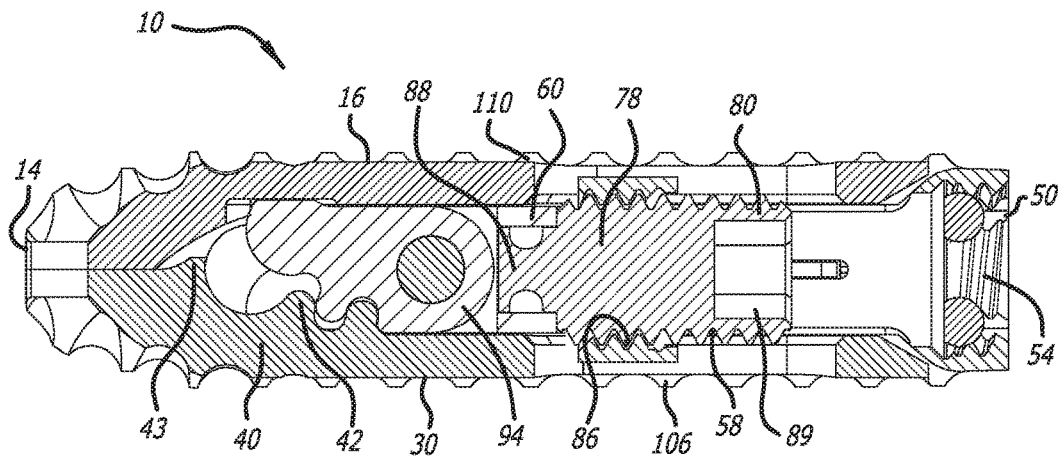
FIG. 8 is a cross-sectional side view of a geared cam expandable spinal implant in accordance with the invention, in a collapsed position.
Figure 9:
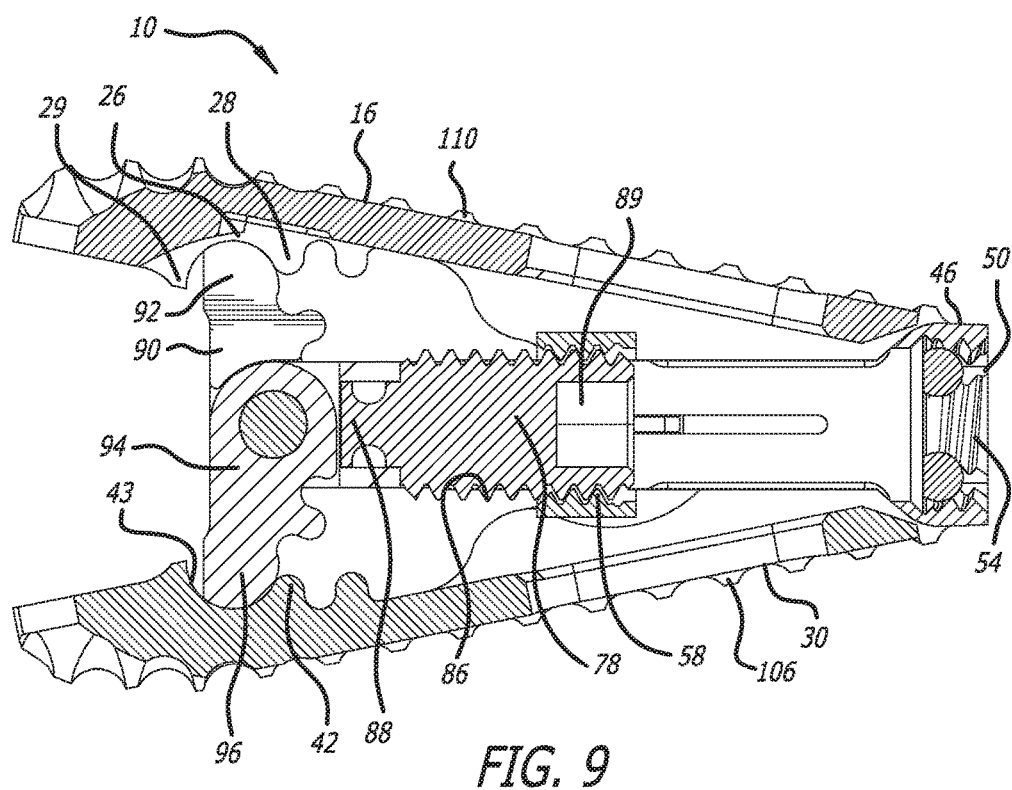
FIG. 9 is a cross-sectional side view of a geared cam expandable spinal implant in accordance with the invention, in a fully-expanded position.

In one embodiment, the implant 10 includes an upper endplate 16. As depicted in FIGS. 6, 8, and 9, the upper endplate 16 includes a proximal end 18, a distal end 20, side surfaces 22, and an inner surface 24. The inner surface 24 includes an upper rack portion 26, which includes downwardly-projecting teeth 28, and a distal-most downwardly-projecting tooth 29.

In one embodiment, the implant 10 includes a lower endplate 30. The lower endplate 30 includes a proximal end 32, a distal end 34, side surfaces 36, and an inner surface 38. The inner surface 38 includes a lower rack portion 40, which includes upwardly-projecting teeth 42, and a distal-most upwardly-projecting tooth 43.

In one embodiment, the implant 10 includes a chassis portion 44 mounted within the implant between the upper endplate 16 and the lower endplate 30. The chassis portion 44 includes a proximal end 46 and a distal end 48. As depicted in FIGS. 7-9, 21, 22, and 46, the proximal end 46 of the chassis portion 44 is a wall perpendicular to the mid-longitudinal axis L-L, having an opening 50 defined through the wall, and one or more depressions 52 defined in the wall proximate the opening 50. The chassis portion 44 further includes a first set of internal threads 54 defined in the opening 50 of the proximal end 46.

In one embodiment, as depicted in FIGS. 1-7, the chassis portion 44 includes an arcuate portion 56 intermediate the proximal end 46 and the distal end 48. A second set of internal threads 58 is defined on an inner surface of the arcuate portion 56.

Figure 5:
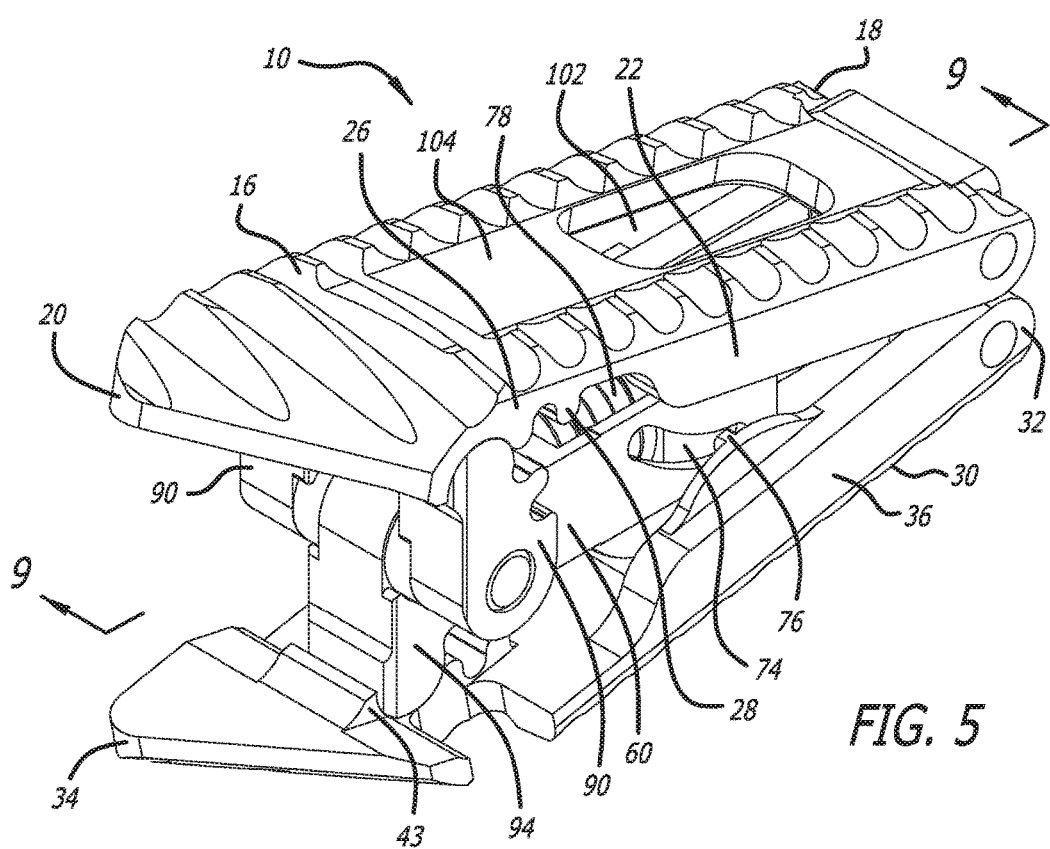
FIG. 5 is an upper perspective view of a geared cam expandable spinal implant in accordance with the invention, in a fully expanded position.

In one embodiment, a yoke 60 is movably mounted within the chassis portion 44. The yoke 60 is defined by a first wall 62, and a parallel second wall 64 spaced away from the first wall 62. First wall 62 has a proximal end 66 and a distal end 68. Second wall 64 has a proximal end 70 and a distal end 72. As depicted in FIGS. 6, 7, and 41-43, distal ends 68 and 72 of first and second walls 62 and 64 can be connected by a distal end cross-piece 71. As depicted in FIG. 5, the yoke 60 includes a slot 74 defined in at least one of first wall 62 and second wall 64. Each slot 74 is configured to receive therein a pin 76 projecting from an inner side surface of the lower endplate 30. Insertion of the pin 76 into the slot 74 assists in preventing separation of the implant 10.

In one embodiment, a rotating portion 78 is rotatably mounted within the chassis portion 44. Rotating portion 78 includes a proximal end 80, a distal end 82, and an outer surface 84, with outer threads 86 defined on the outer surface 84. In one embodiment, as depicted in FIGS. 6, 8, 9, 20-22, 25-27, 30, and 31, the distal end 82 includes a T-shaped projection 88. The invention, however, is not limited to having a T-shaped projection at the distal end 82 of the rotating portion 78. In one embodiment, the proximal end 80 of the rotating portion includes an opening 89, configured to receive therein a distal end of an implant expansion tool (not shown). The invention is not limited to any particular configuration for the opening 89, as long as the rotating portion 78 can be rotated by the implant expansion tool. As depicted in FIGS. 8 and 9, the opening 89 has a polygonal shape to receive a polygonal-shaped distal end of the implant expansion tool. As another example, but not by way of limitation, the opening 89 could be threaded to receive a threaded distal end of the implant expansion tool.

Figure 47:
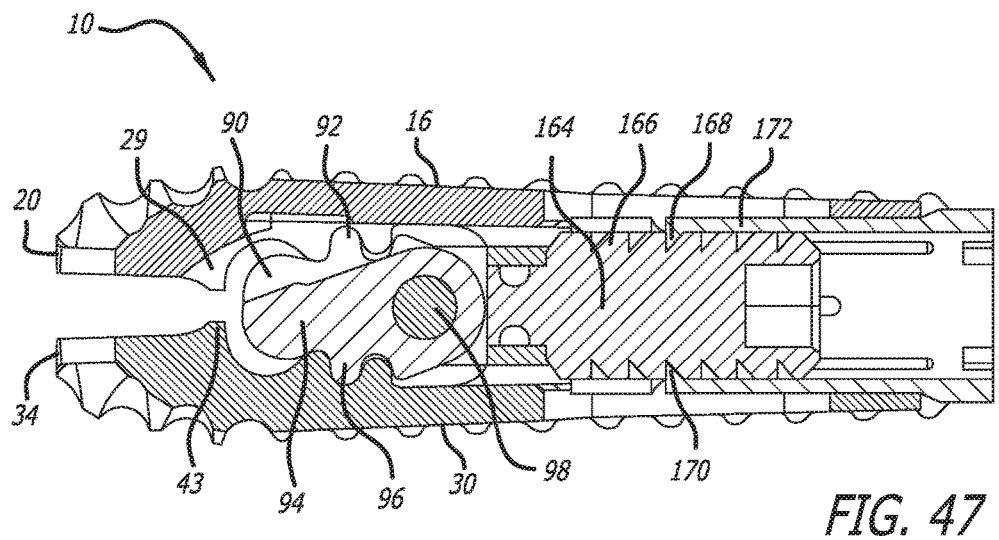
FIG. 47 is a side cross-sectional view of a geared cam expandable spinal implant in accordance with the invention.
Figure 48:
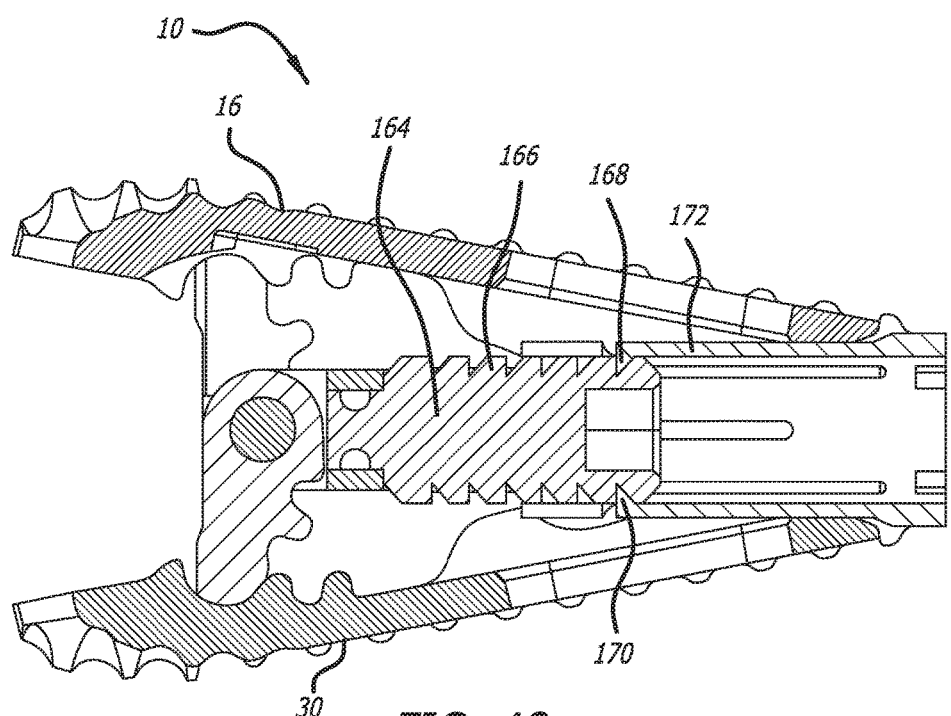
FIG. 48 is a side cross-sectional view of a geared cam expandable spinal implant in accordance with the invention.
Figure 49:
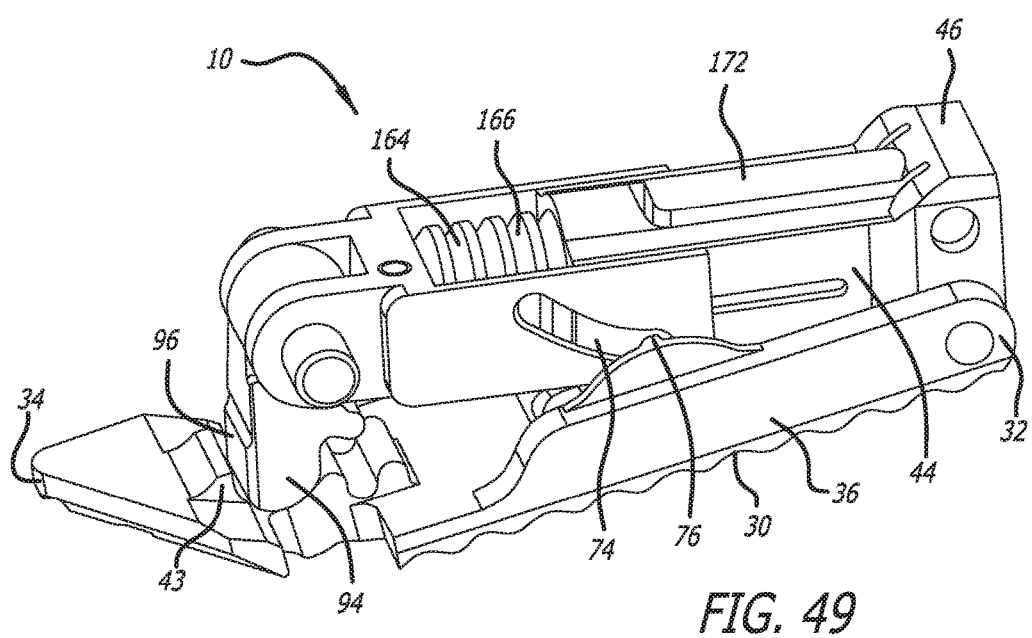
FIG. 49 is a partial upper perspective view depicting a lower endplate, chassis, yoke, lower spur gear, and cylinder with circumferential ratchet teeth.

In one embodiment, as depicted in FIG. 47-49, the threaded rotating portion 78 has been replaced by a cylinder 164 with circumferential ratchet teeth 166, and the mating threads 54 on the arcuate portion 56 have been replaced by integral pawls 168. The ratchet teeth 166 are separated by grooves 170. The pawls 168 are allowed to flex because they are integral with "live" springs 172 attached to the chassis portion 44. In this embodiment, as the ribbed cylinder 164 is advanced, each pawl 168 advances to the next respective groove 170. In this manner, the distal end of the cylinder 164 pushes on the yoke 60, causing the spur gears 90 and 94 to walk toward the distal end 14 of the implant 10, expanding the implant, while the pawls 168 are retained in the respective grooves 170 between the ratchet teeth 166, thereby retaining the implant 10 in its current expanded position.

In one embodiment, a pair of first spur gears 90 is rotatably mounted to the distal end 68 of the first wall 62 of the yoke 60, and the distal end 72 of the second wall 64 of the yoke 60, respectively. Each first spur gear 90 includes projecting first spur gear teeth 92, configured to engage with the downwardly-projecting teeth 28 of the upper rack portion 26.

Figure 20:
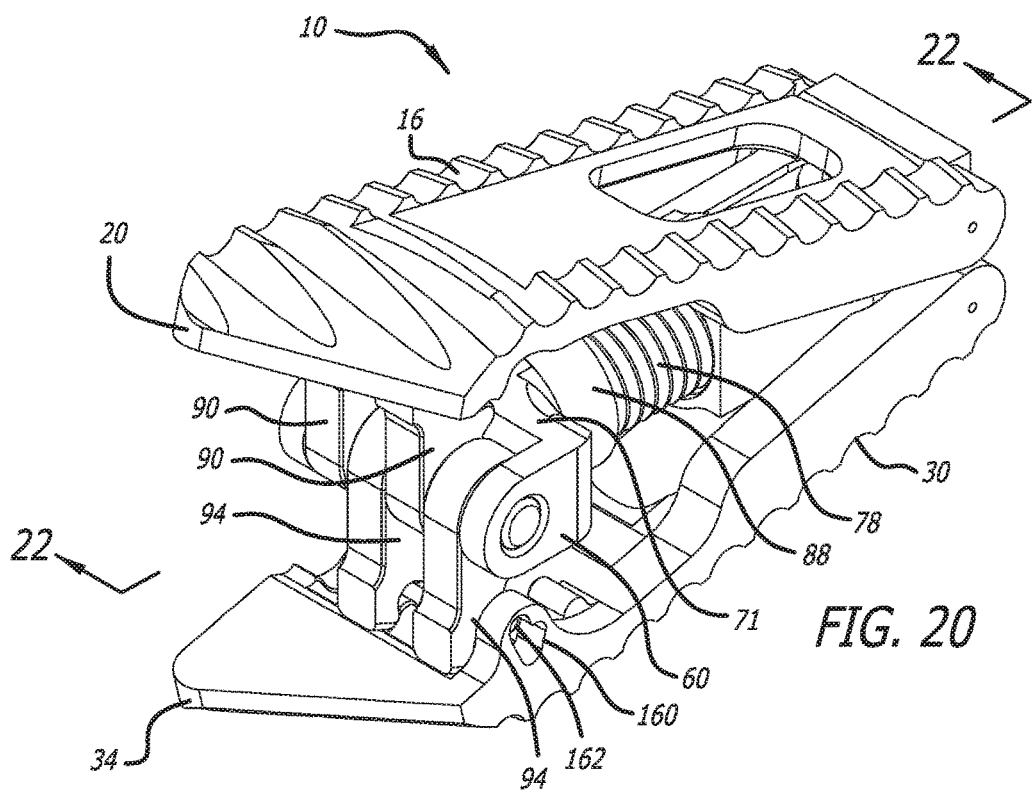
FIG. 20 is an upper perspective view of a geared cam expandable spinal implant in accordance with the invention, in a fully expanded position.
Figure 21:
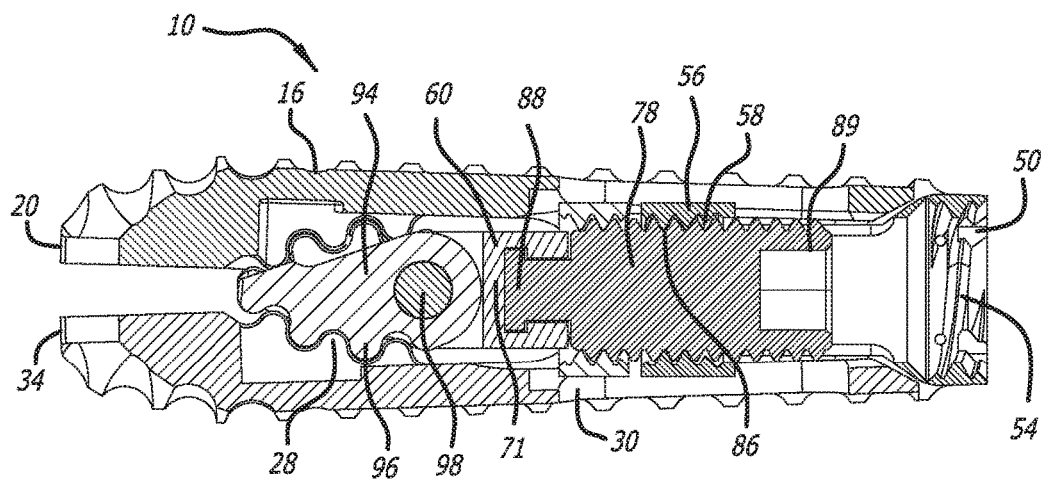
FIG. 21 is a side cross-sectional view of a geared cam expandable spinal implant in accordance with the invention, in a partially expanded position.
Figure 22:
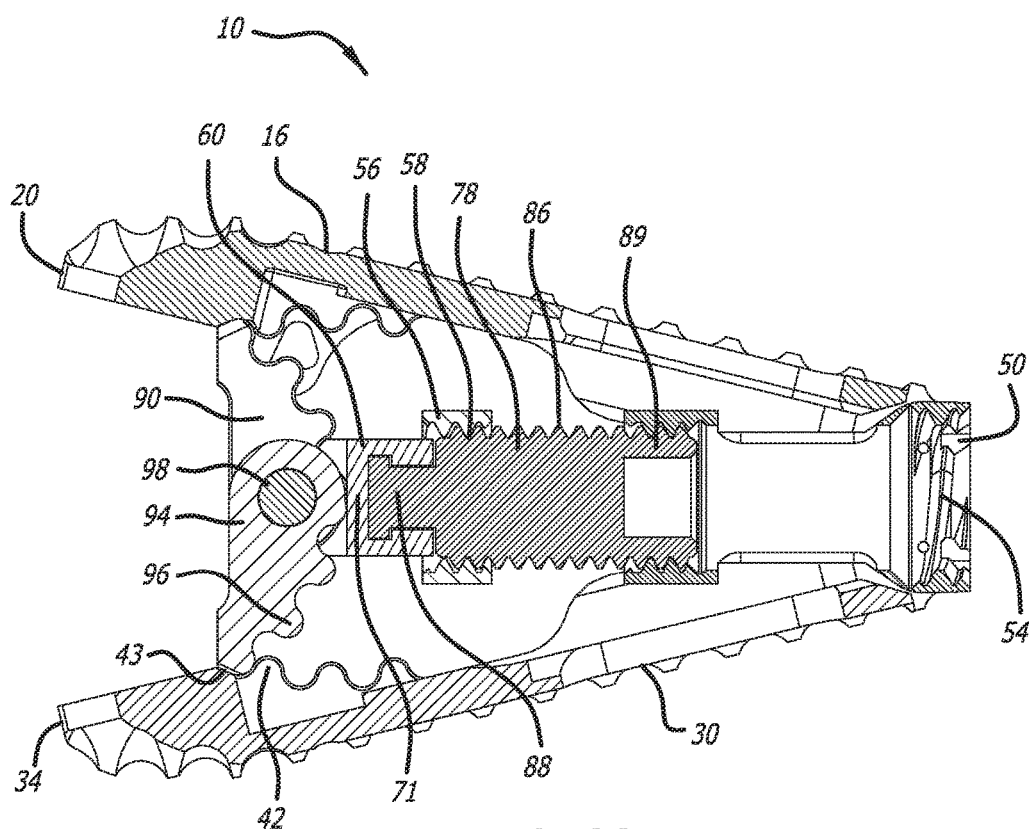
FIG. 22 is a side cross-sectional view of a geared cam expandable spinal implant in accordance with the invention, in a fully expanded position.

In one embodiment, as depicted in FIGS. 5-7, 18, 24, 36, and 37, a second spur gear 94 is rotatably mounted between the distal end 68 of the first wall 62 of the yoke 60, and the distal end 72 of the second wall 64 of the yoke 60, respectively. As depicted in FIG. 6, the spur gears 90 and 94 are rotatably attached to the yoke 60 with a pin 98. The second spur gear 94 includes projecting second spur gear teeth 96, configured to engage with the upwardly-projecting teeth 42 of the lower rack portion 40. The invention is not limited to having two first spur gears 90 and one second spur gear 94. For example, as depicted in FIG. 20, the invention can include two first spur gears 90 and two second spur gears 94. It is also within the scope of the invention to have one first spur gear 90, and two second spur gears 94.

Figure 19:
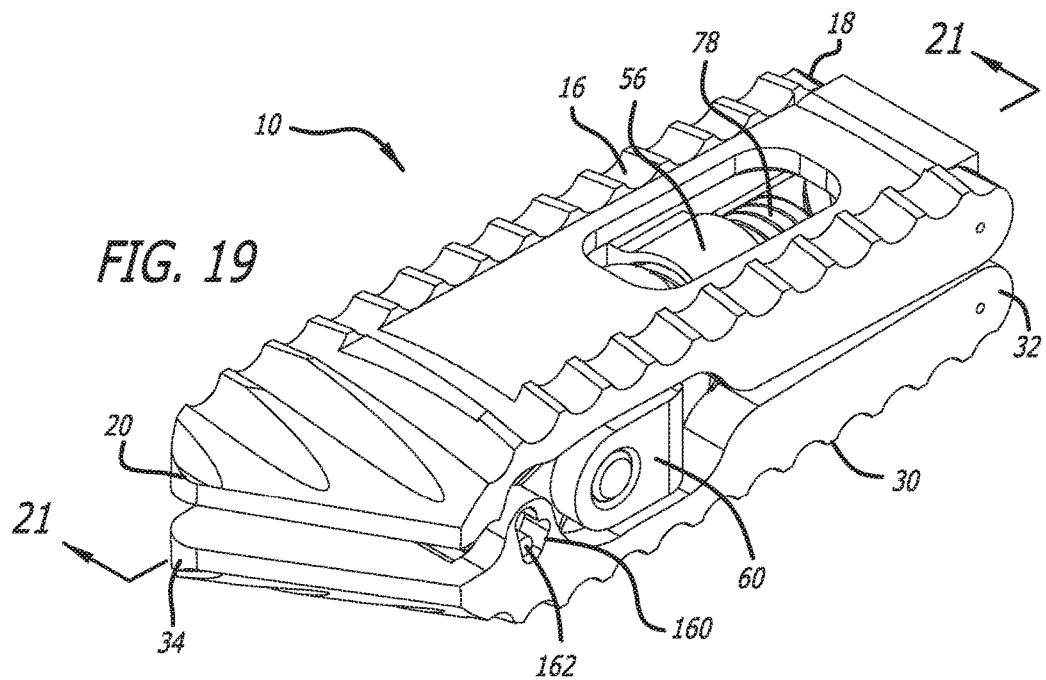
FIG. 19 is an upper perspective view of a geared cam expandable spinal implant in accordance with the invention, in a partially expanded position.

In one embodiment, as depicted in FIGS. 19 and 20, a slot 160 is defined in the side surface 36 proximate the distal end 34 of the lower endplate 30, and a pin 162 is defined projecting from a second spur gear 94. Pin 162 is configured to engage with slot 160, to help prevent the upper and lower endplates from separating.

In one embodiment, the rotating portion 78 rotates within the chassis portion 44, with the outer threads 86 of the rotating portion 78 engaging threaded portion 58 of the chassis portion 44, until the distal end 82 of the rotating portion 78 contacts the distal cross-piece 71 of the yoke 60. Rotation of the rotating portion 78 is translated into linear motion of the yoke 60 towards the distal end 14 of the implant 10. Linear motion of the yoke 60 causes the first spur gears 90, and the second spur gears 94 to rotate. The respective first spur gear teeth 92 and second spur gear teeth 96 "walk" towards the distal end 14 of the implant 10 in the respective downwardly-projecting teeth 28 of the upper rack portion 26, and upwardly-projecting teeth 42 of the lower rack portion 40. As the teeth "walk," the upper endplate 16 is moved away from the lower endplate 30, thereby moving the implant 10 into and through the partially-expanded position. When the respective spur gear teeth 92 and 96 reach the respective distal-most downwardly-projecting tooth 29, or alternately the distal-most upwardly-projecting tooth 43, they can "walk" no farther towards the distal end of the implant 10, and the implant has reached the fully-expanded position. The amount of expansion in the fully-expanded position is related to the length of the spur gears. As depicted in FIG. 6, the spur gears have a length S1, but different spur gear lengths are possible, depending on the requirements of an individual patient. Different amounts of full expansion, related to spur gear length are depicted, for example, in FIGS. 4, 5, 9, 20, and 22.

Figure 32:
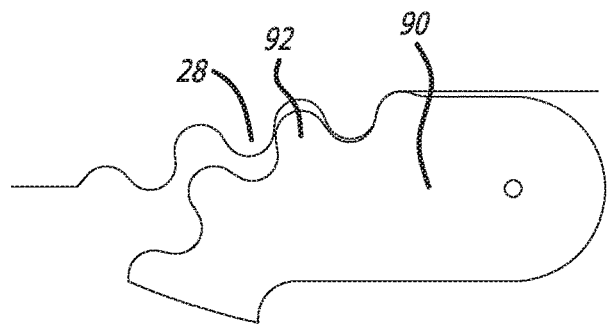
FIGS. 32-34 are side schematic views of a spur gear and rack in a one-stage expansion mechanism.
Figure 33:
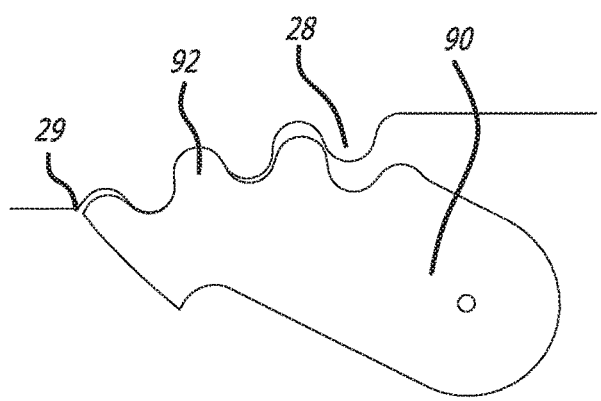
Figure 34:
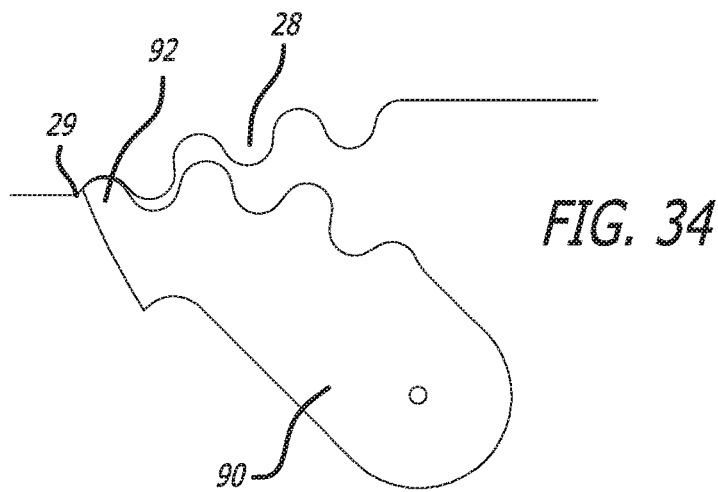
Figure 37:
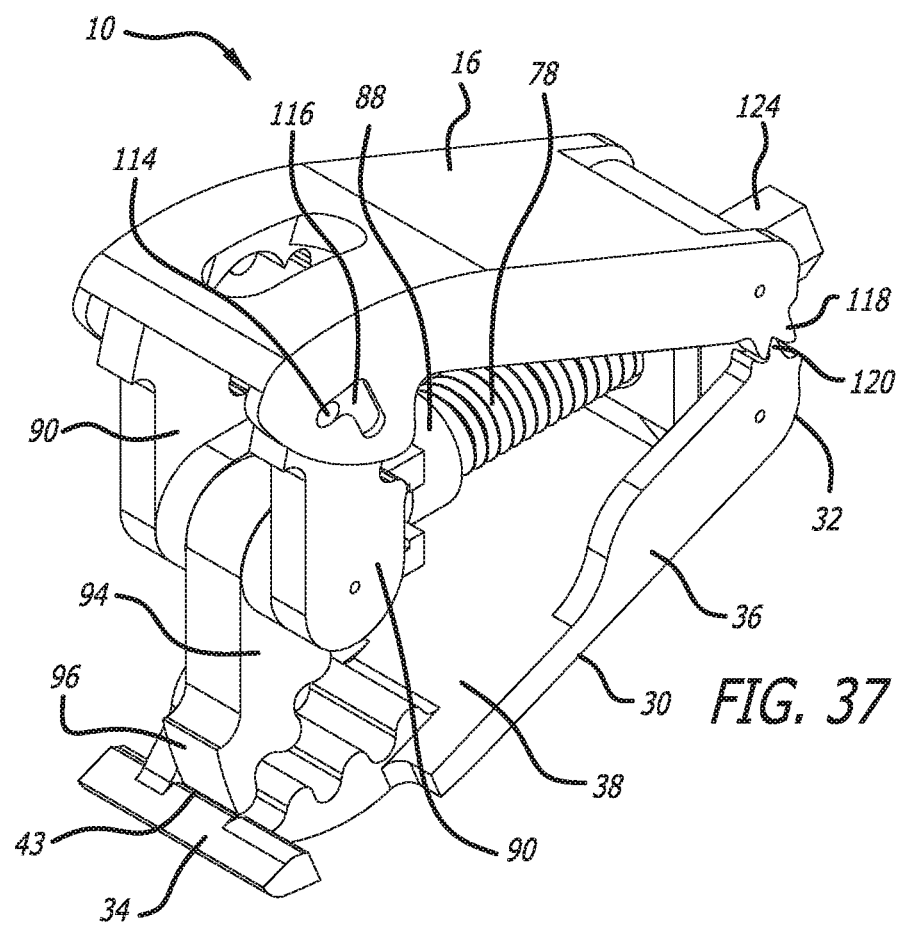
FIG. 37 is an upper perspective view of a geared cam expandable spinal implant in accordance with the invention in a fully expanded position.

In one embodiment, as depicted in FIGS. 32-34, the spur gears 90 and 94 "walk" along the respective racks 26 and 40 in a one-stage expansion movement, with the respective spur simply rolling along the respective rack.

Figure 14:
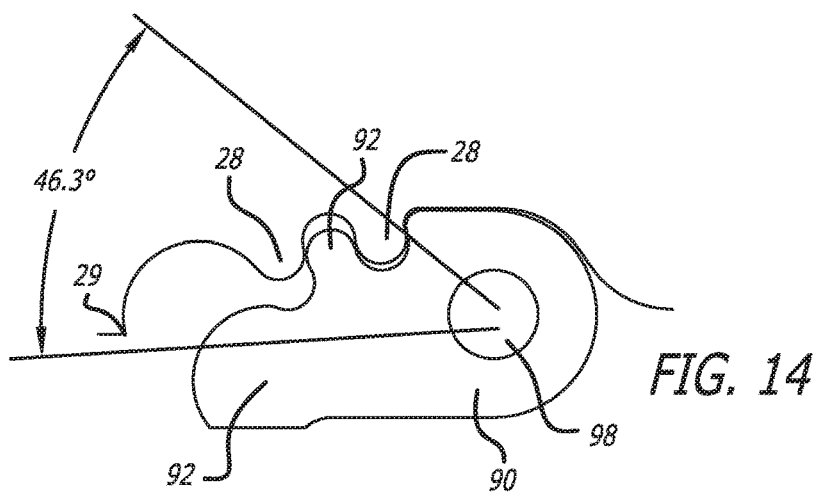
Figure 15:
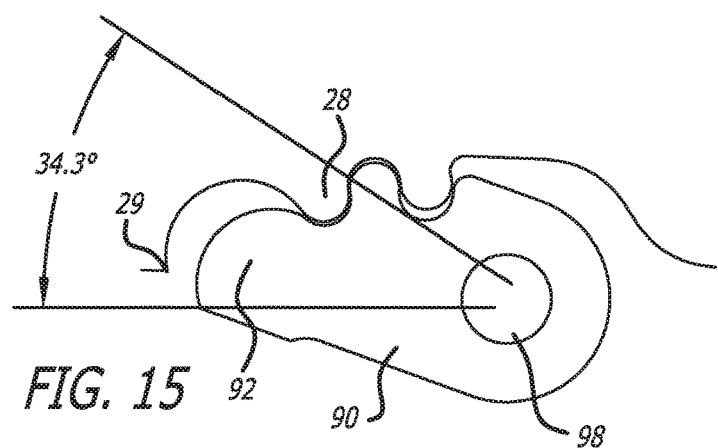
Figure 16:
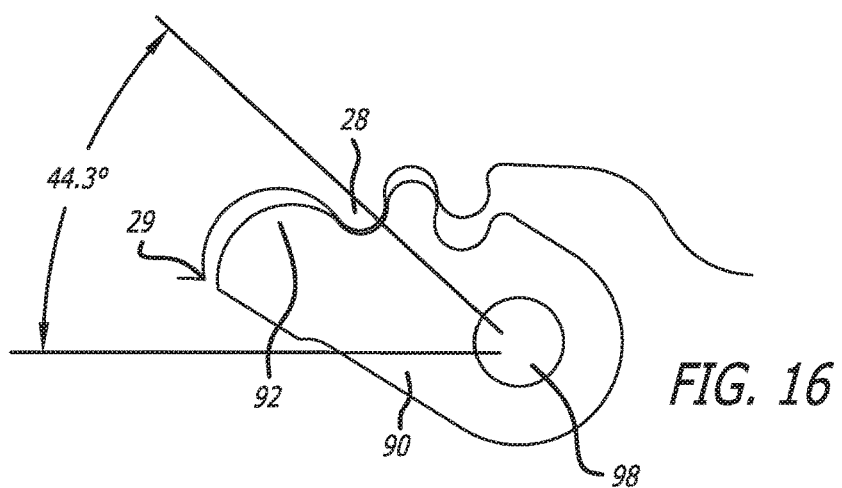
Figure 17:
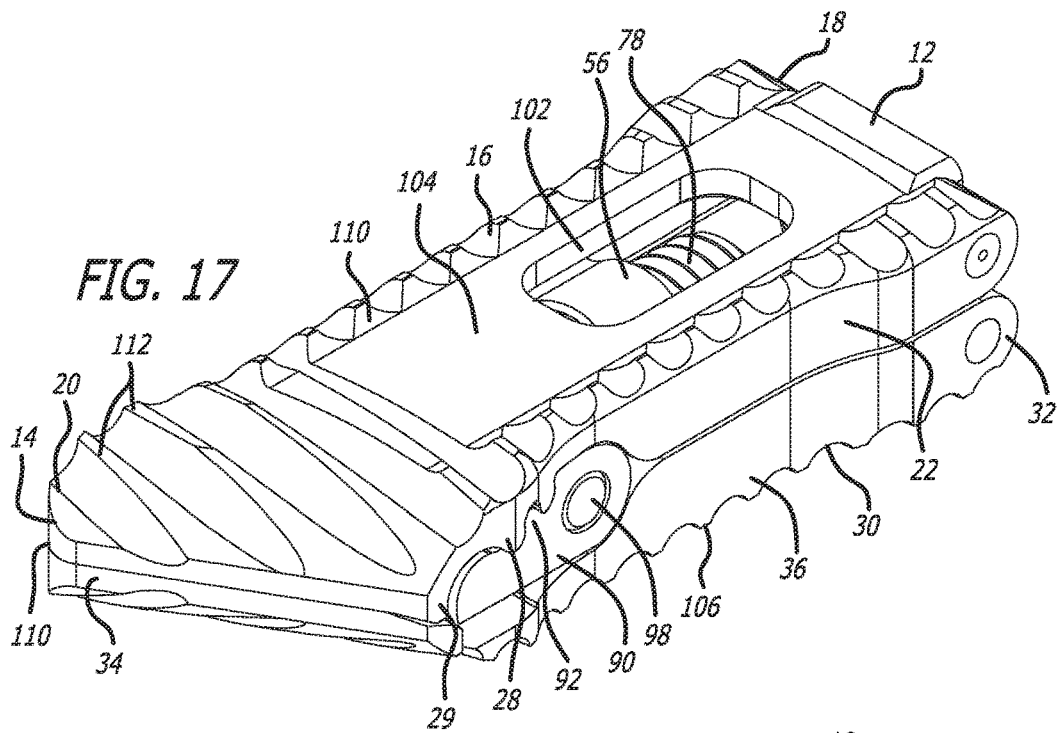
FIG. 17 is an upper perspective view of a geared cam expandable spinal implant in accordance with the invention, in a collapsed position.
Figure 18:
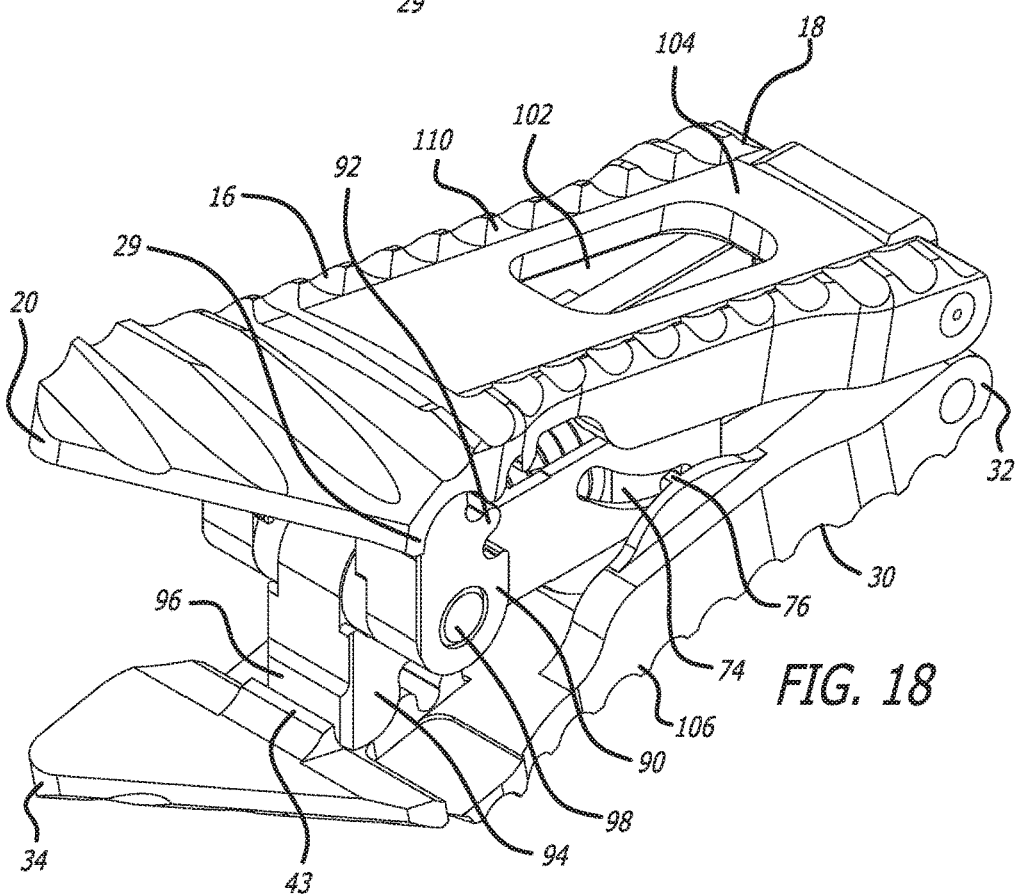
FIG. 18 is an upper perspective view of a geared cam expandable spinal implant in accordance with the invention, in a fully open position.

In one embodiment, as depicted in FIGS. 10-16, the spur gears 90 and 94 "walk" along the respective racks 26 and 40 in a multi-stage expansion movement, including the respective spur initially rolling along the respective rack, as depicted in FIGS. 10 and 11, and subsequently pivoting in a ball and socket fashion, as depicted in FIGS. 12 and 13. As depicted in FIGS. 14-16, the circumferences of the pitch diameters translate along each other as the gear is advanced. This translation allows a higher angle of incidence at the starting point for the device as compared to a fixed-length link mechanism. The angle of incidence/mechanical advantage starts high and decreases as the gear is advanced, increasing as the gear advances further. The multi-stage expansion pattern allows a constant angle of attack of the gear with the rack.

Figure 1:
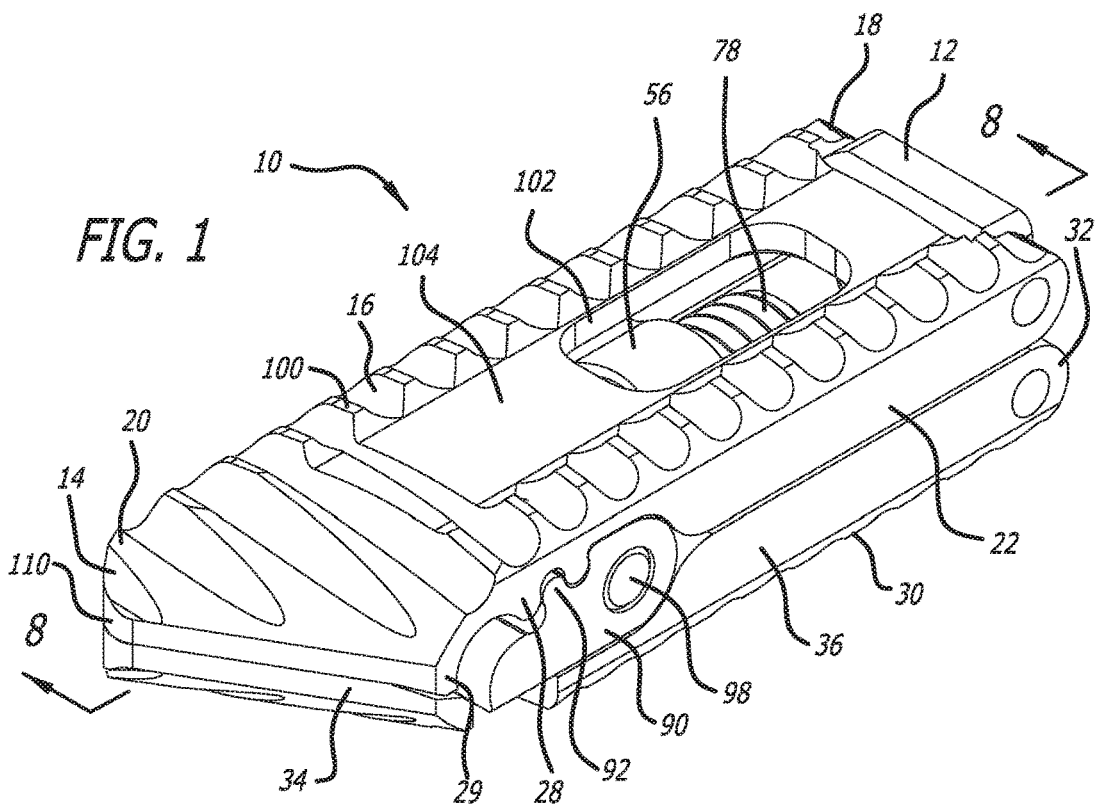
FIG. 1 is an upper perspective view of a geared cam expandable spinal implant in accordance with the invention, in a collapsed position.
Figure 2:
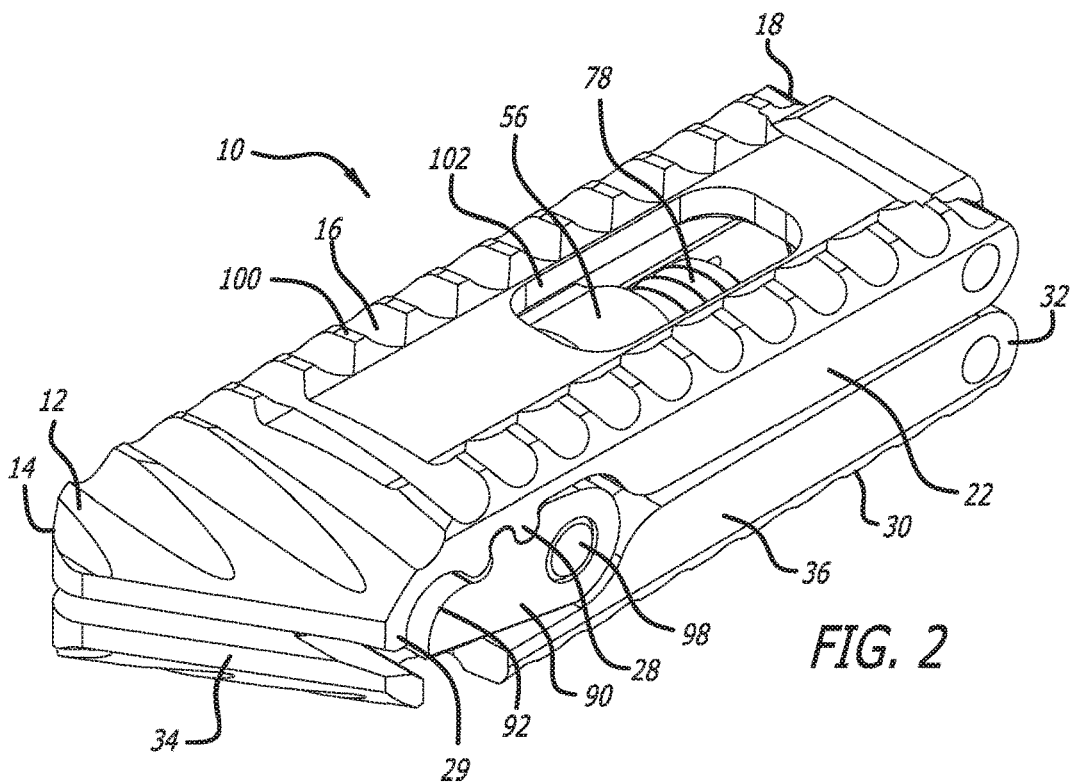
FIG. 2 is an upper perspective view of a geared cam expandable spinal implant in accordance with the invention, in a partially expanded position.
Figure 3:
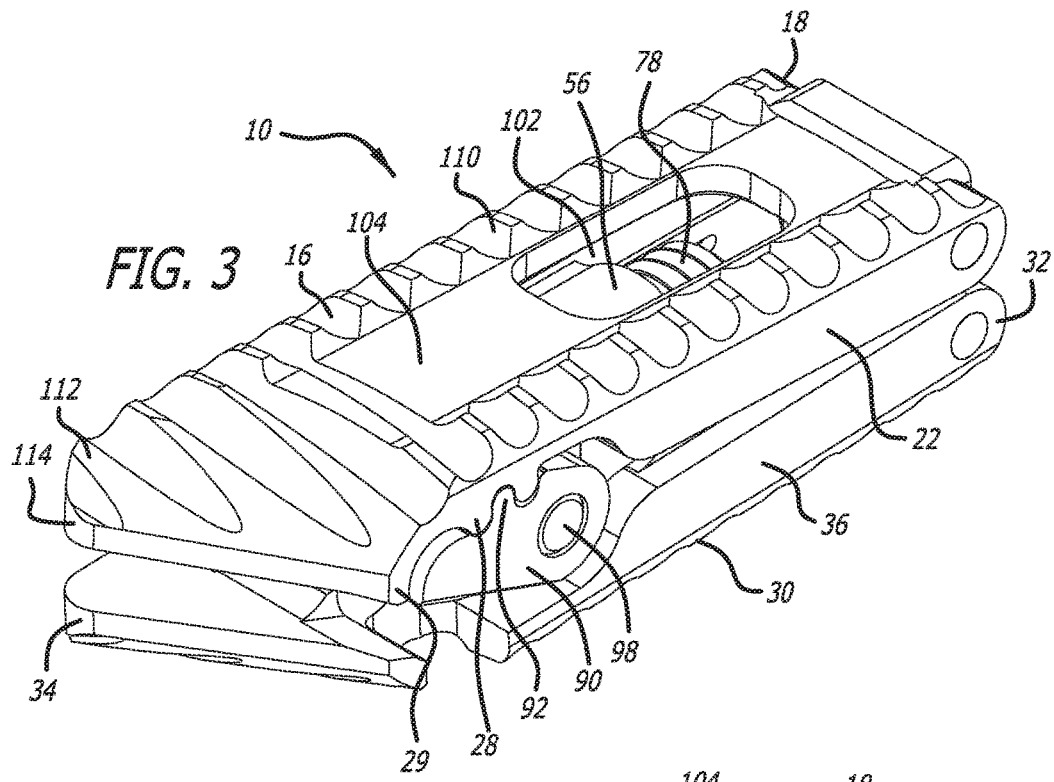
FIG. 3 is an upper perspective view of a geared cam expandable spinal implant in accordance with the invention, in a partially expanded position.
Figure 4:
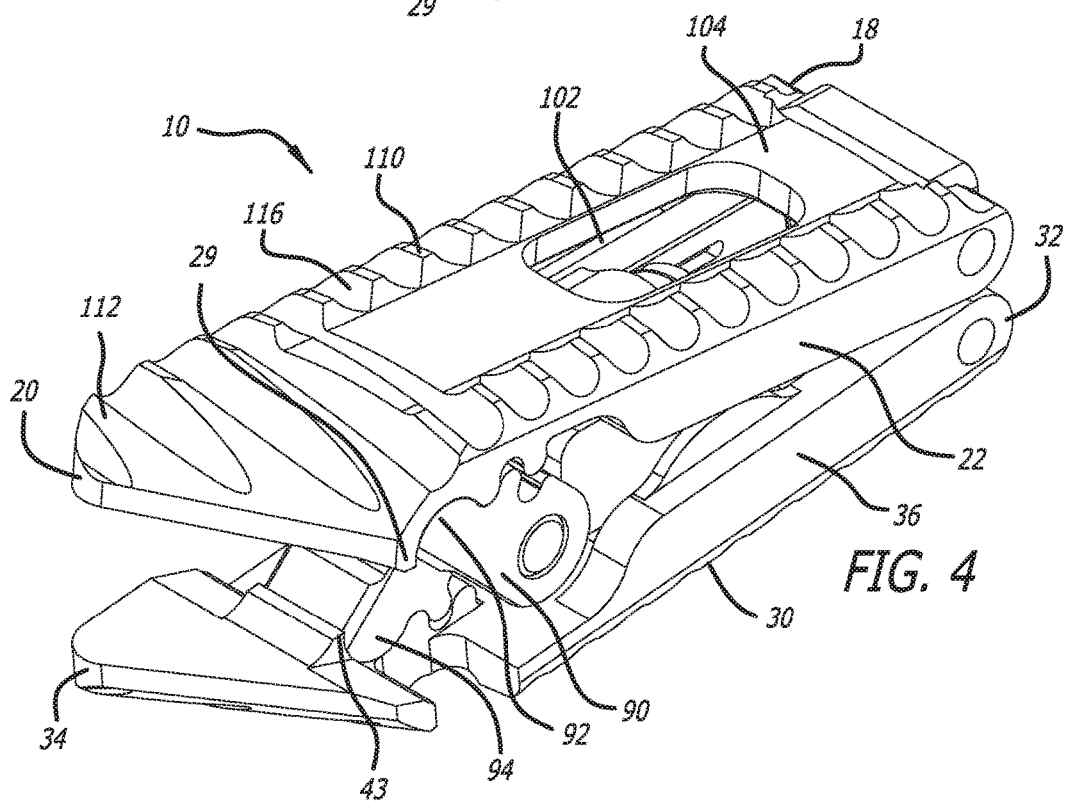
FIG. 4 is an upper perspective view of a geared cam expandable spinal implant in accordance with the invention, in a fully expanded position.

In one embodiment, as depicted in FIGS. 1 and 2, the upper endplate 16 includes projections 100, configured to engage a surface of the endplate of the upper vertebral body (not shown). The upper endplate 16 further includes an opening 102 defined therein, configured to allow bone growth from bone growth material loaded in the implant 10 to pass through the opening 102 and fuse with the upper vertebral body. The upper endplate 16 further includes a smooth surface 104, configured to distribute the vertebral body endplate loading. The smooth surfaces 104 can be configured along a majority of the length of the upper surface of the upper endplate 16, as depicted in FIGS. 1 and 2, or for only a portion of the length of the upper surface, to contact only the softer cancellous-like bone off the upper vertebral body endplate.

In one embodiment, as depicted in FIGS. 8 and 9, the lower endplate 30 includes projections 106 for engaging the endplate of the lower vertebral body (depicted in FIG. 45), and an opening 108 configured to allow bone growth from the bone graft material in the implant 10 to pass through the opening 108 and fuse with the lower vertebral body.

Figure 23:
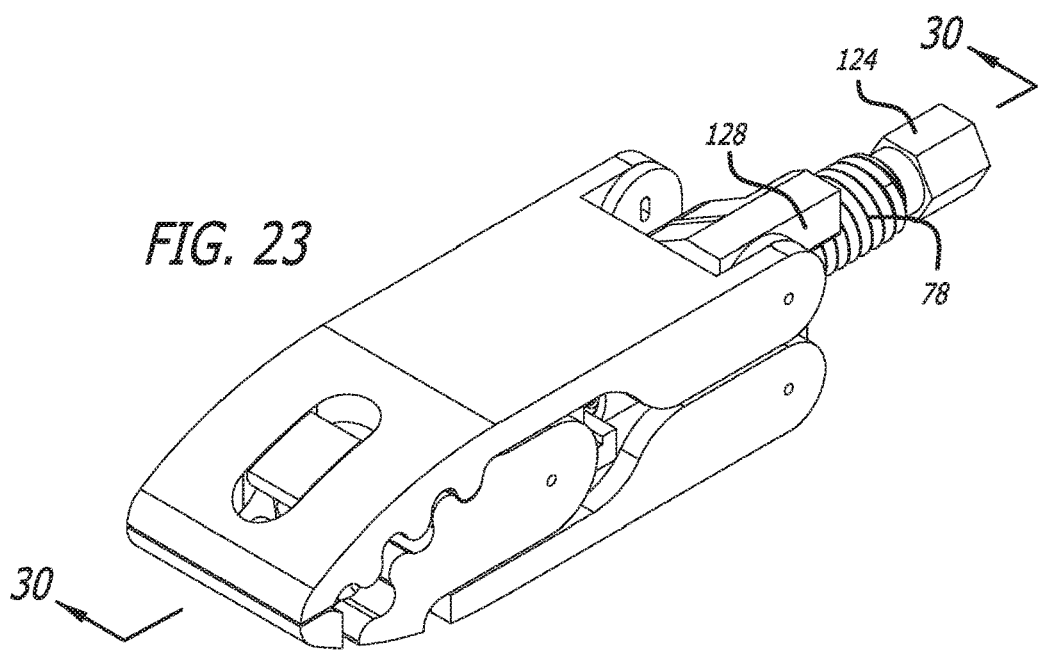
FIG. 23 is an upper perspective view of another embodiment of a geared cam expandable spinal implant in accordance with the invention, in a collapsed position.
Figure 24:
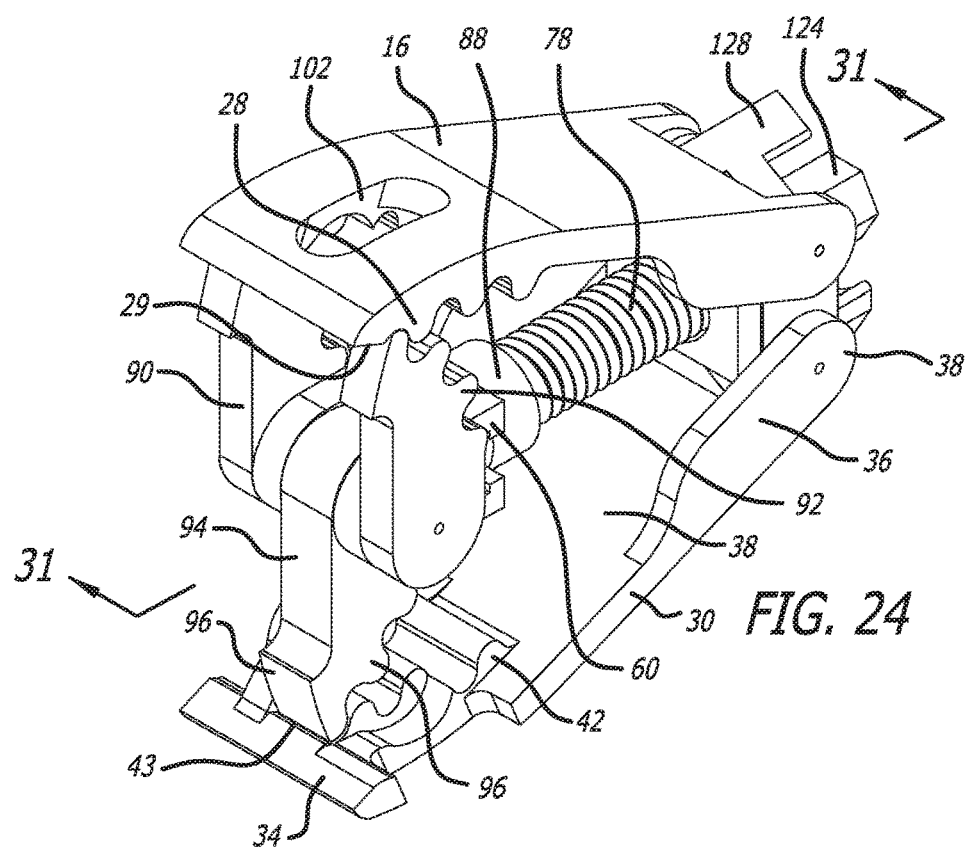
FIG. 24 is an upper perspective view of the embodiment of FIG. 23, in a fully expanded position.
Figure 25:
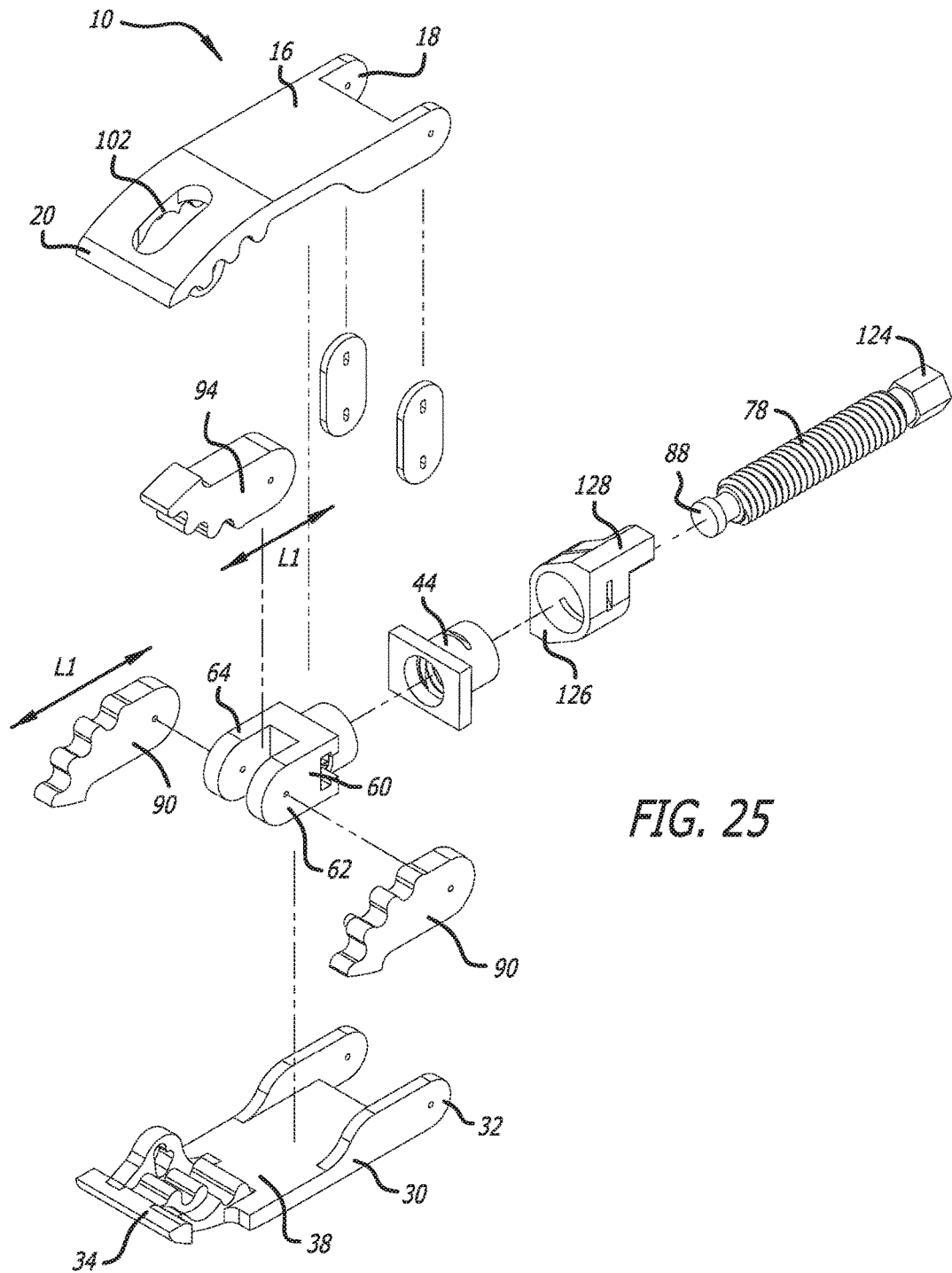
FIG. 25 is an exploded parts view of a geared cam expandable implant in accordance with the invention.
Figure 26:
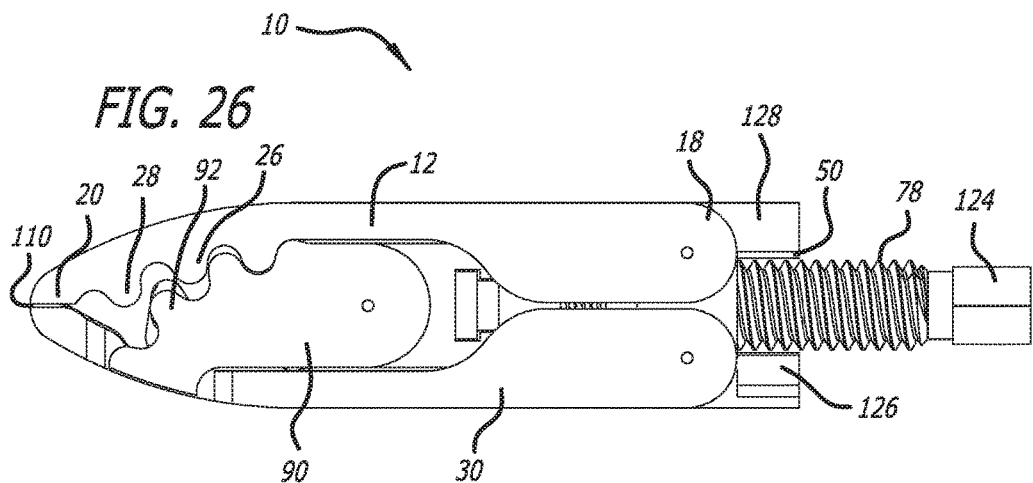
FIG. 26 is a side cross-sectional view of a geared cam expandable spinal implant in accordance with the invention, in a collapsed position.
Figure 27:
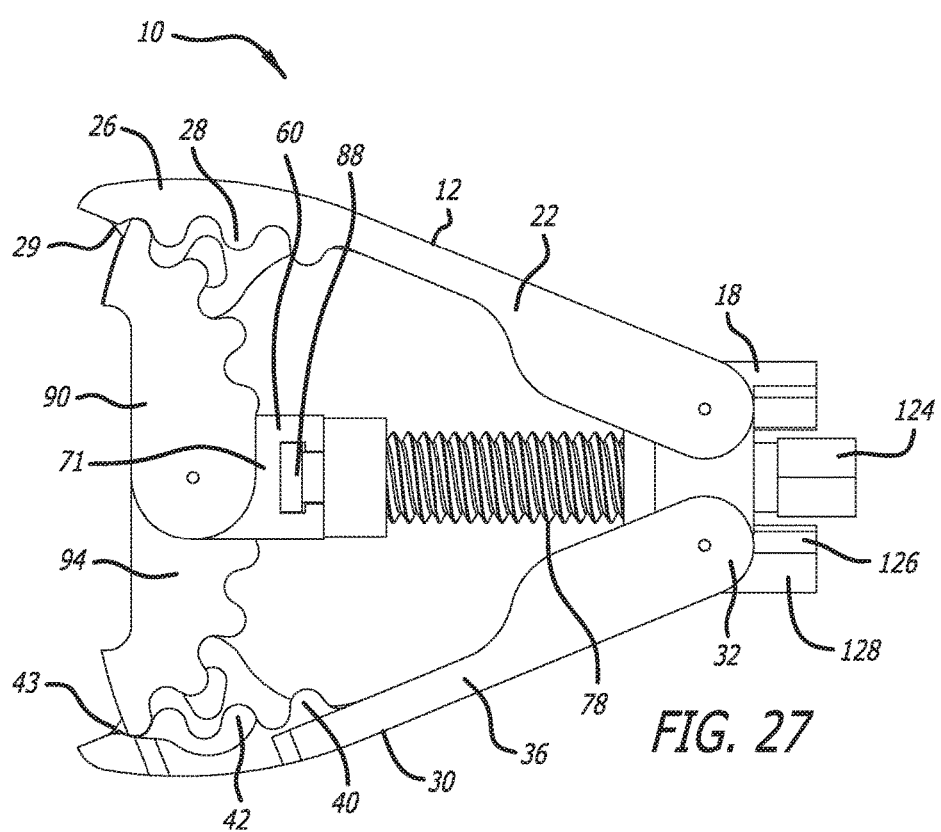
FIG. 27 is a side cross-sectional view of a geared cam expandable spinal implant in accordance with the invention in a fully expanded position.
Figure 28:
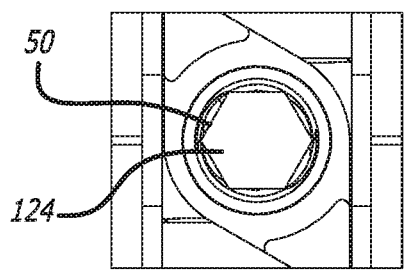
FIGS. 28 and 29 are rear views of a geared cam expandable spinal implant in accordance with the invention.
Figure 29:
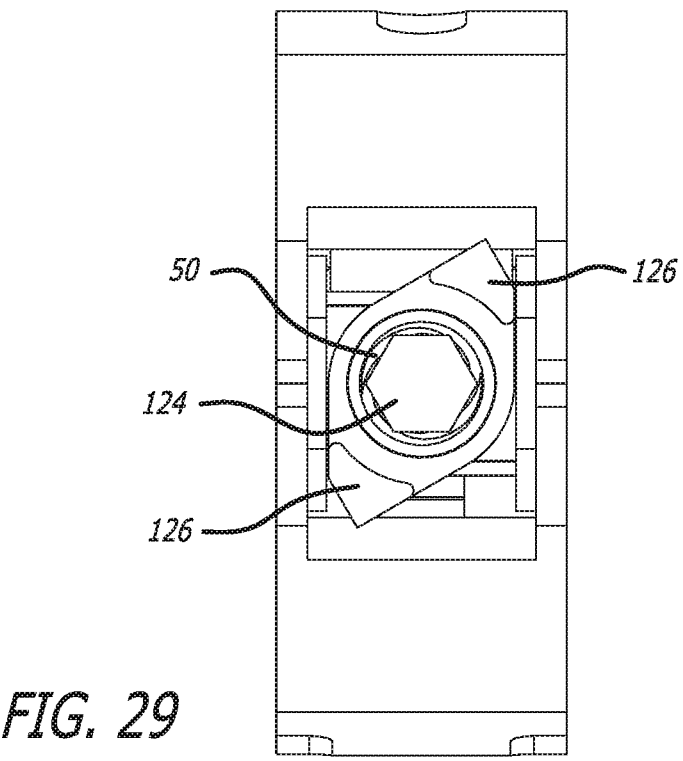
Figure 30:
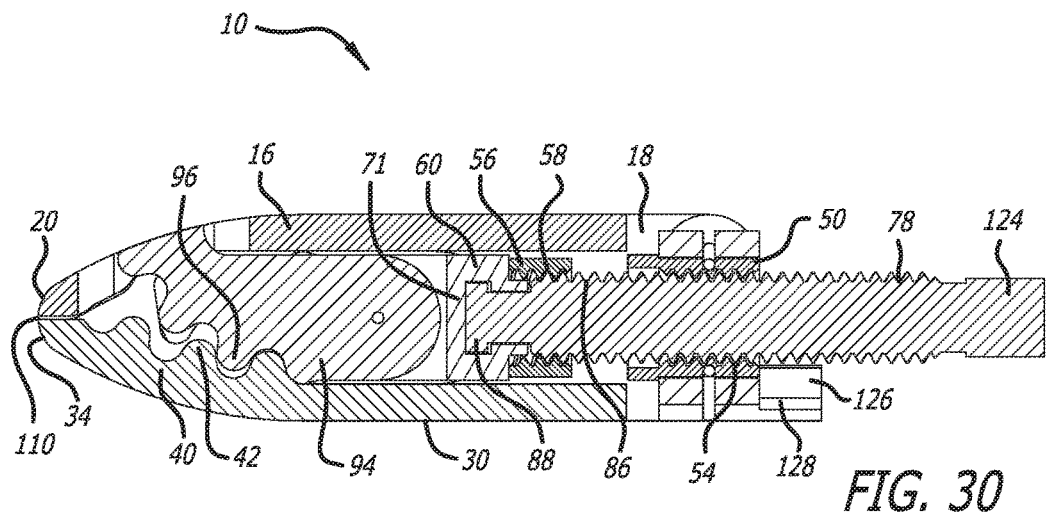
FIG. 30 is a side cross-sectional view of a geared cam expandable spinal implant in accordance with the invention in a collapsed position.
Figure 31:
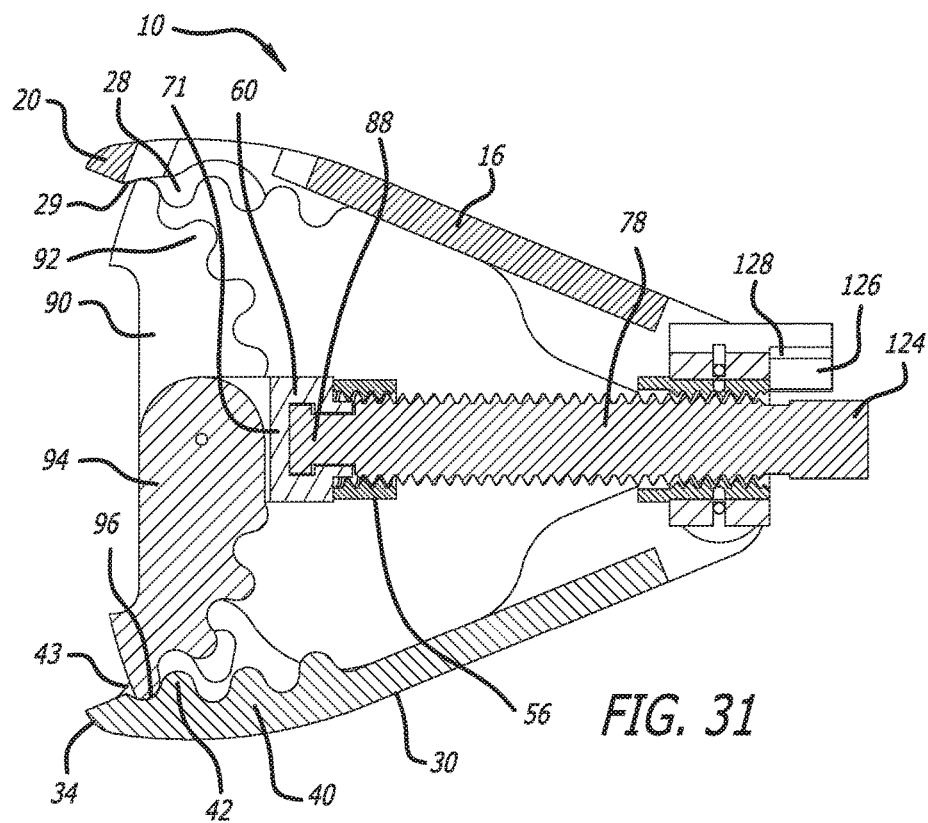
FIG. 31 is a side cross-sectional view of a geared cam expandable spinal implant in accordance with the invention in a fully expanded position.
Figure 45:
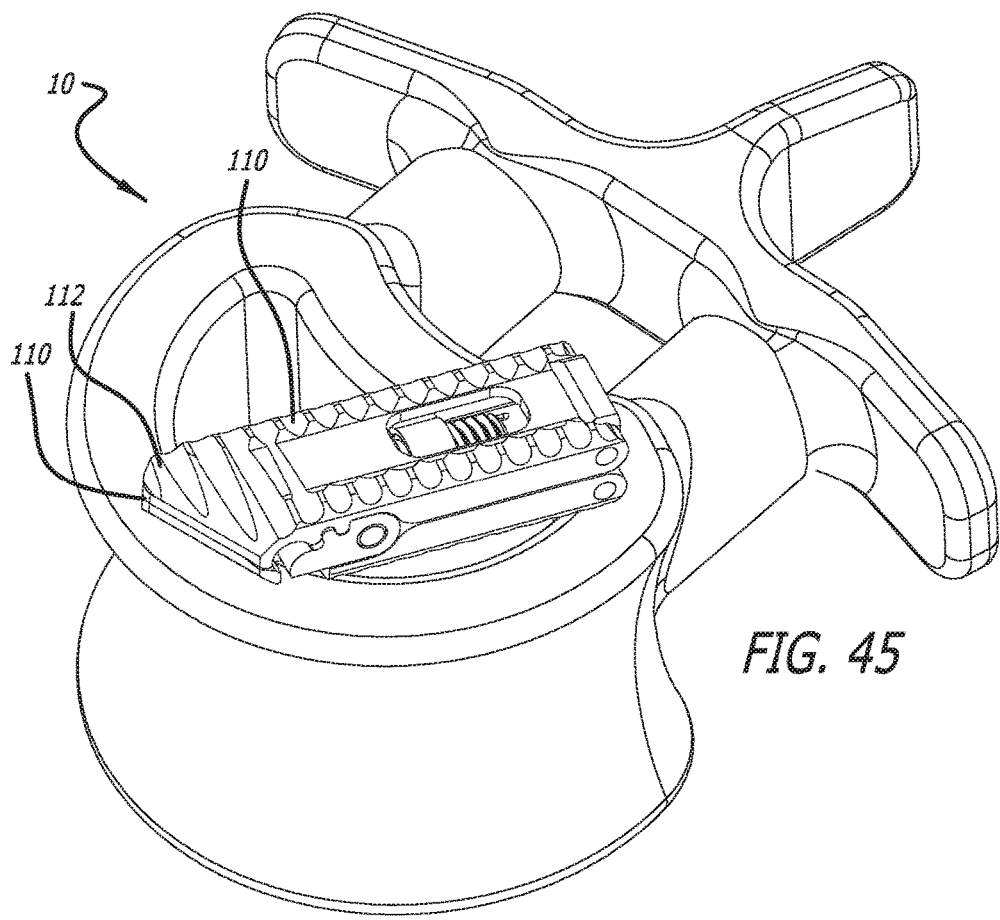
FIG. 45 is an upper perspective view of a geared cam expandable implant in accordance with the invention being supported by a lower vertebral body.

In one embodiment, the distal end 20 of the upper endplate 16, and the distal end 34 of the lower endplate 30 define a tip 110. The tip 110 can be beveled, as depicted in FIG. 45; flat, as depicted in FIGS. 23 and 24; or come to a central point, as depicted in FIG. 26.

In one embodiment, the tip 110 can include bone-engaging projections 112. In accordance with another embodiment, the tip 110 can have no projections. The bone-engaging projections 112 are configured to prevent implant migration as the implant 10 is expanding. The bone-engaging projections 112 may be perpendicular to the side surfaces 22 and 36, but generally follow the shape of the tip 110, or they could be parallel to the tip 110.

In one embodiment as depicted in FIGS. 35 and 36, an engaging pin 114 extends from at least one spur gear 90 or 94, and is engaged in a slot 116 in a side of the upper endplate 16. Engagement of the engaging pin 114 in slot 116 assists in preventing the endplates 16 and 30 from decoupling during expansion of the implant 10.

In one embodiment, as depicted in FIGS. 35 and 36, an upper gear 118 is defined at the proximal end 18 of the upper endplate 16, in engagement with a lower gear 120 defined at the proximal end 32 of the lower endplate 30. Engagement of the upper and lower proximal gears 118 and 120, respectively, assists in preventing the endplates 16 and 30 from decoupling during expansion of the implant 10.

In one embodiment, an independent proximal expansion mechanism 122 is defined at the proximal end 12 of the implant 10. As depicted in FIGS. 28-31, 35, and 36, the proximal expansion mechanism 122 includes a proximal-end polygonal-shaped toggle 124, attached to the proximal end 80 of the rotating portion 78. A pair of proximal-end pivot pins 126 projects from the proximal-end toggle 124. In one embodiment, the toggle 124 can have one distraction position while in another embodiment, the toggle 124 can have progressive distraction positions. In one embodiment, the toggle 124 can be rotated, while in another embodiment, the toggle 124 can be translated. In the embodiment where the toggle 124 is rotated, the pivot pins 126 distract, using a cam-like action. In the embodiment where the toggle 124 is translated, the pivot pins 126 are distracted by sliding along proximal ramps 128.

In one embodiment, an insertion tool 130, depicted in FIGS. 38-44 and 46, includes a proximal end 132, and a distal end 134. An outer hollow cylindrical shaft 136 extends between the proximal end 132 and the distal end 134. An inner hollow cylindrical shaft 138 extends through the outer shaft 136. The inner shaft 138 has a proximal end 140 and a distal end 142.

Figure 38:
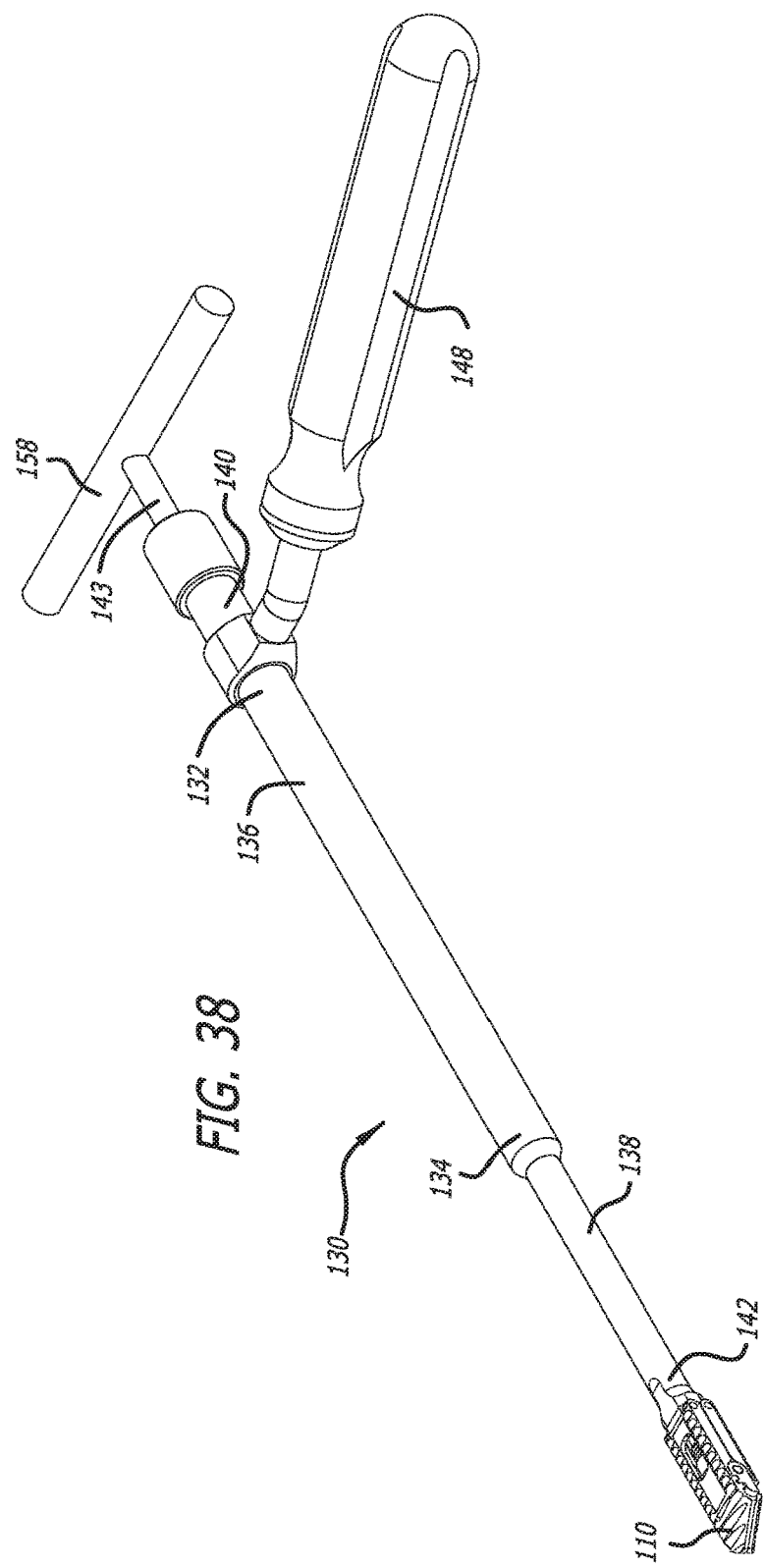
FIG. 38 is an upper perspective cross-sectional view of an implant insertion tool in accordance with the invention connected to a geared cam expandable spinal implant in accordance with the invention.

In one embodiment, as depicted in FIG. 38, a T-handle 158 is defined at the proximal end 140 of the inner shaft 138. The T-handle 158 attaches to an elongated driver 143, which extends through the inner shaft 138.

Figure 42:
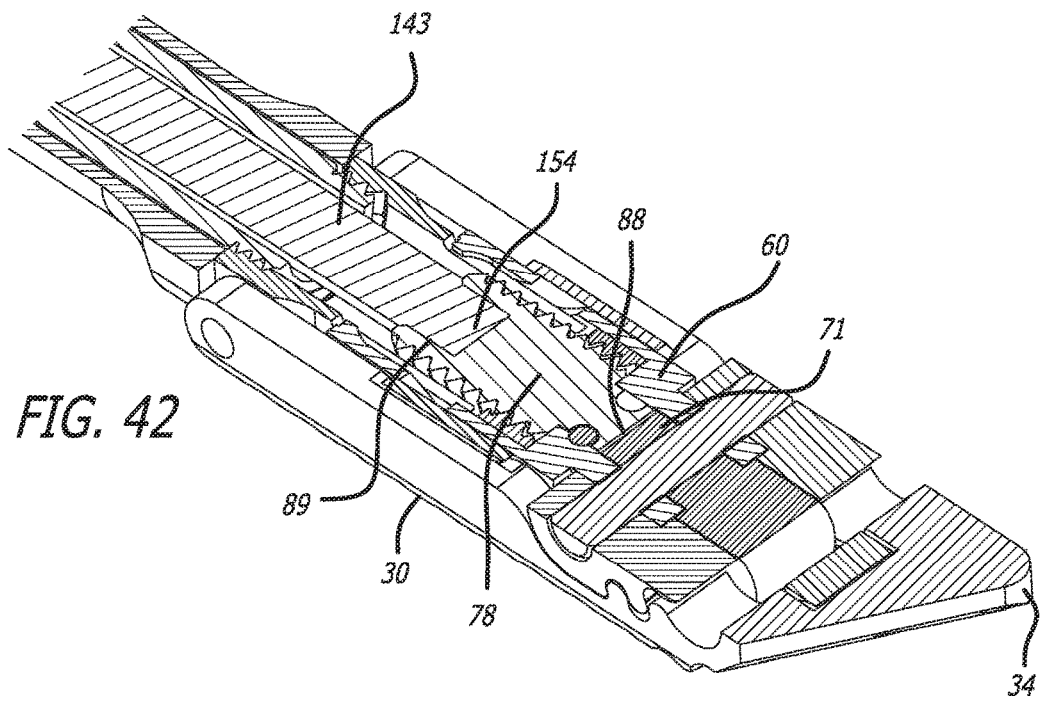
FIG. 42 is an upper perspective cross sectional view of a geared cam expandable implant in accordance with the invention being inserted into a disc space by an implant insertion tool in accordance with the invention.
Figure 43:
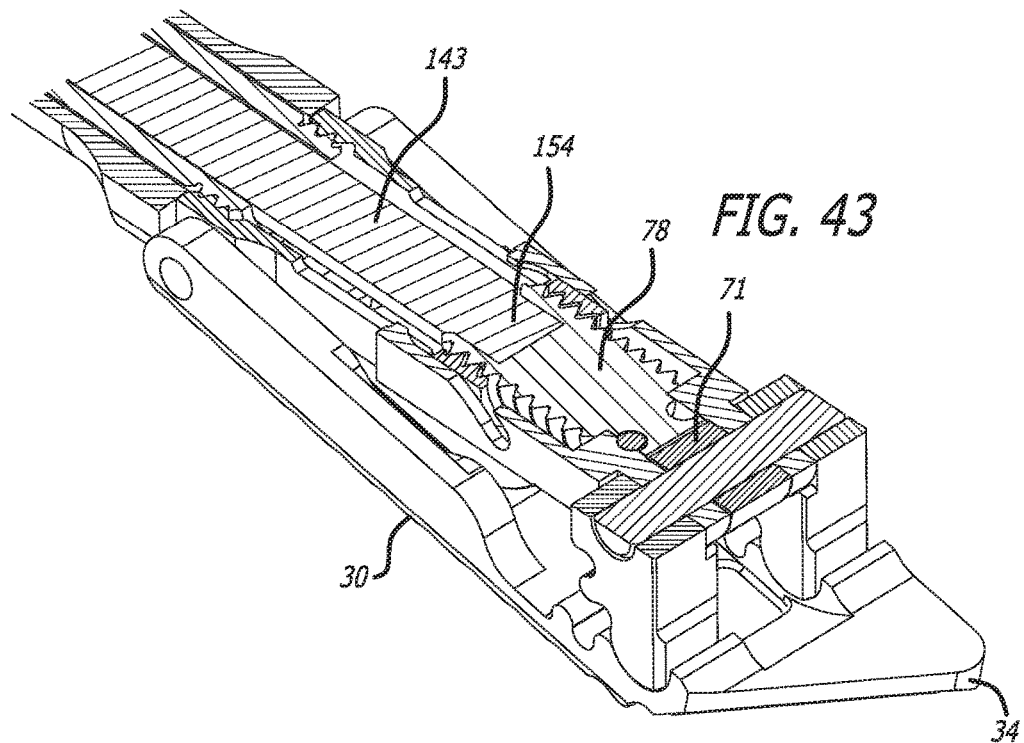
FIG. 43 is an upper perspective cross sectional view of a geared cam expandable implant in accordance with the invention being inserted into a disc space by an implant insertion tool in accordance with the invention.

In one embodiment, as depicted in FIGS. 42 and 43, the elongated driver 143 has a blunt distal end 154.

Figure 39:
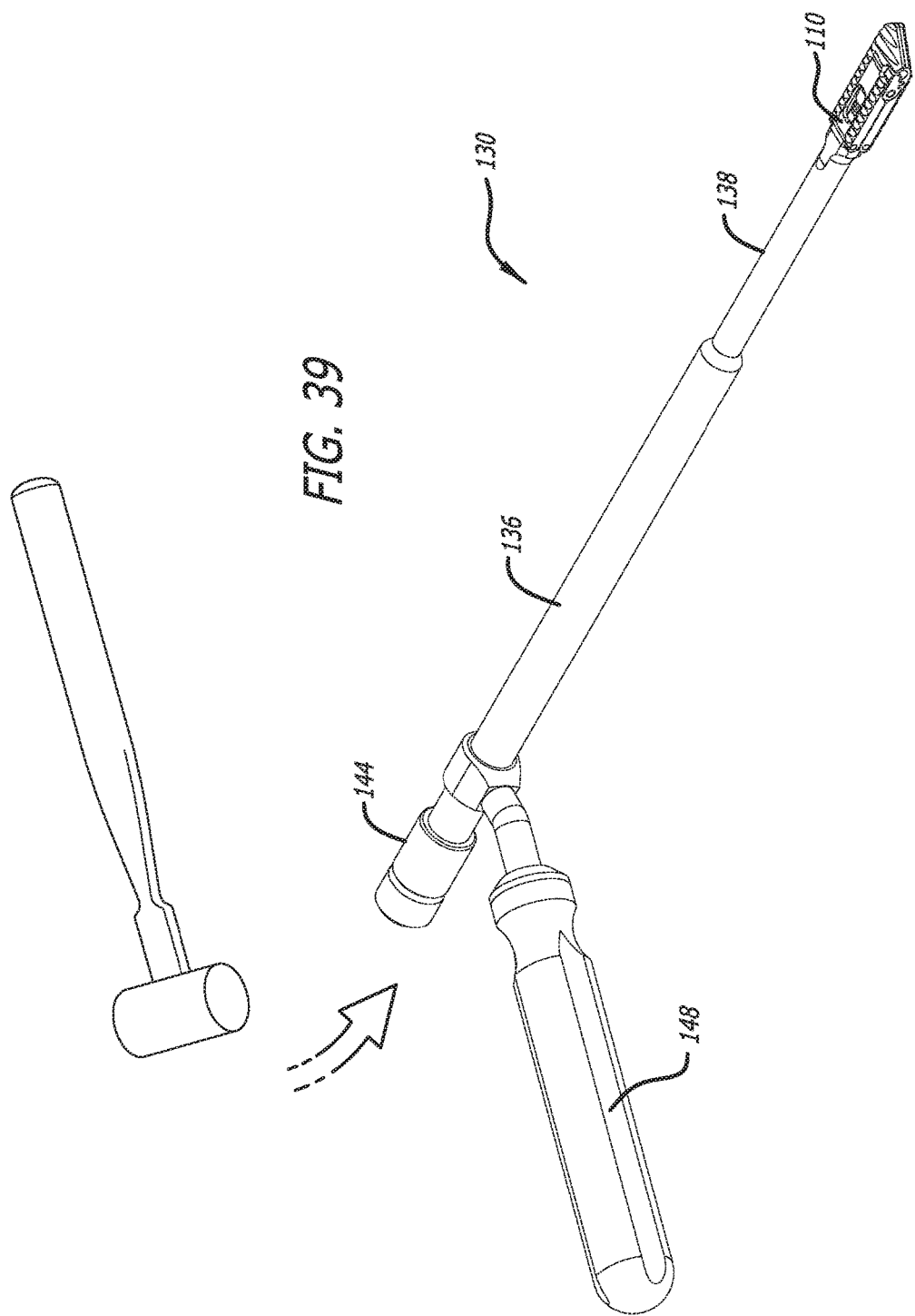
FIG. 39 is an upper perspective view of an implant insertion tool in accordance with the invention connected to a geared cam expandable spinal implant in accordance with the invention, depicting insertion of the implant into a disc space.

In one embodiment, as depicted in FIG. 39, a tap cap 144 is defined at the proximal end 140 of the inner shaft 138, attached to the driver 143.

Figure 40:
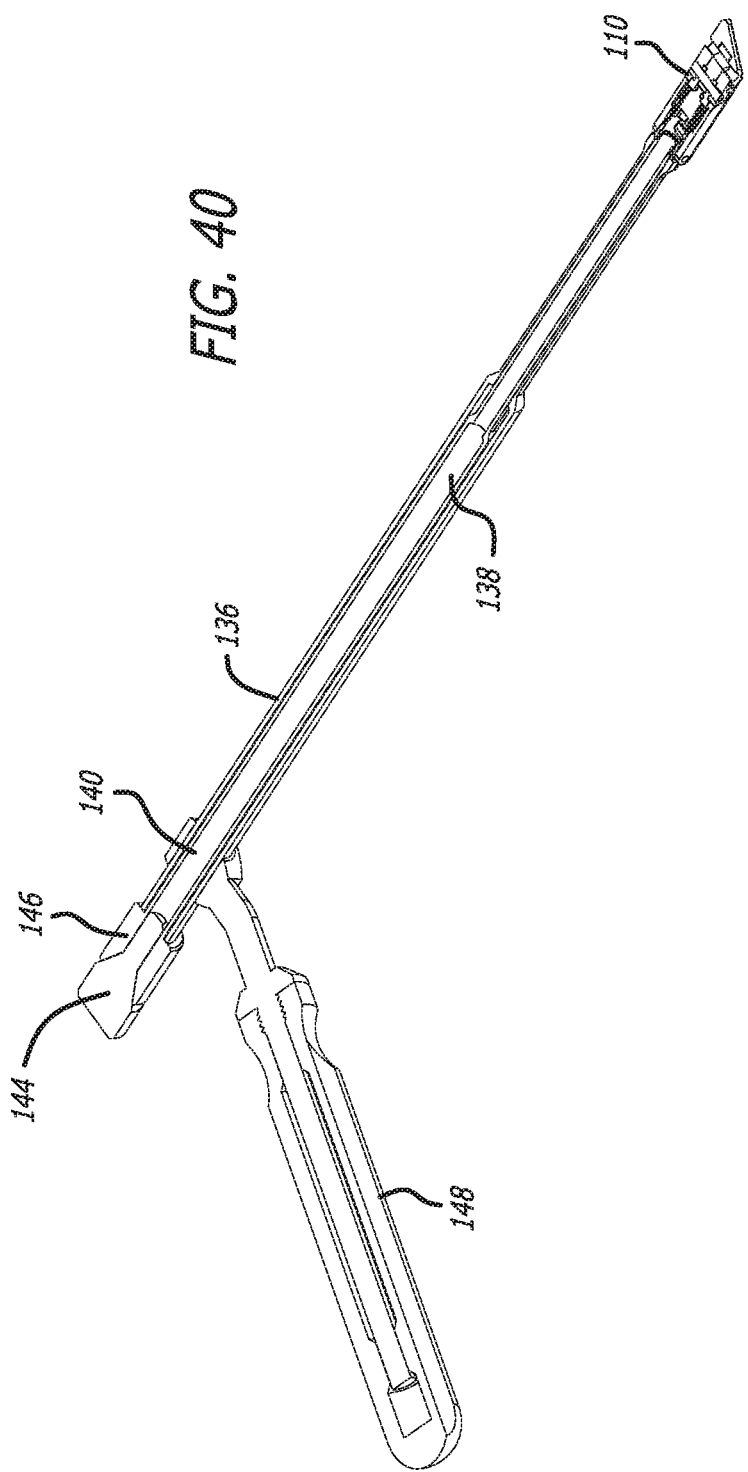
FIG. 40 is an upper perspective cross-sectional view of an implant insertion tool in accordance with the invention connected to a geared cam expandable spinal implant in accordance with the invention.
Figure 41:
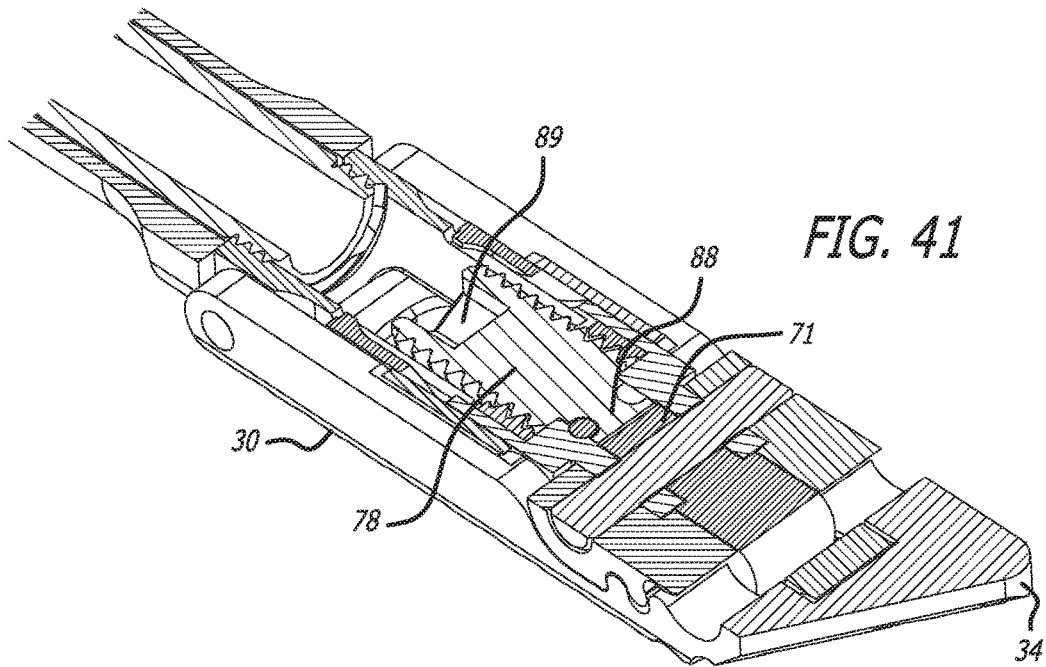
FIG. 41 is an upper perspective cross-sectional view of a geared cam expandable implant attached to an implant insertion tool in accordance with the invention.

In one embodiment, as depicted in FIG. 40, the tap cap 144 fits removably into a funnel 146 defined at the proximal end 140 of the inner shaft 138.

In one embodiment, a handle 148 is provided, gripping an outer surface of the outer shaft 136. Handle 148 is configured to be held by a surgeon while using the insertion tool 130.

Figure 46:
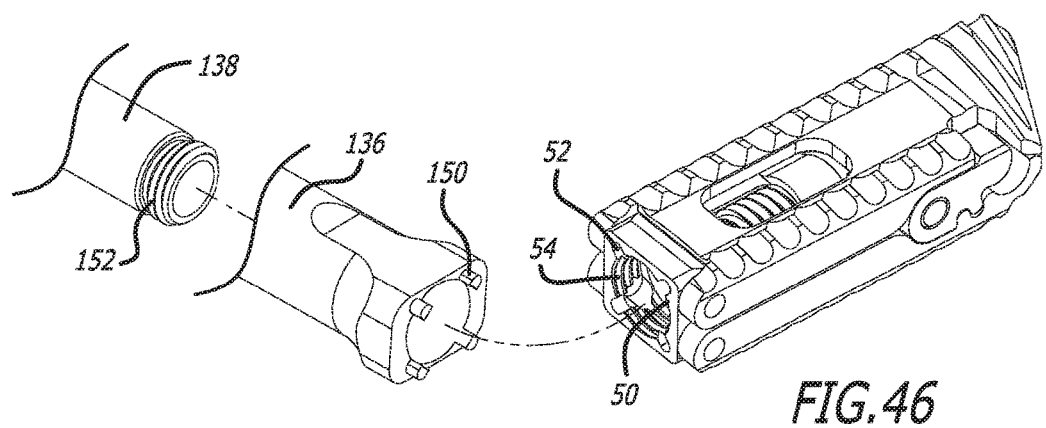
FIG. 46 is an upper perspective view depicting points of attachment between a geared cam expandable implant in accordance with the invention, and an implant insertion tool in accordance with the invention.

In one embodiment, as depicted in FIG. 46, the distal end 134 of the outer shaft 136 includes projecting fingers 150, configured to fit into the depressions 52, proximate the opening 50 in the proximal end 46 of the chassis portion 44.

In one embodiment, as depicted in FIGS. 40 and 46, the distal end 142 of the inner shaft 138 includes external threads 152, configured to engage the first set of inner threads 54 in the opening 50 of the chassis portion 44.

Figure 44:
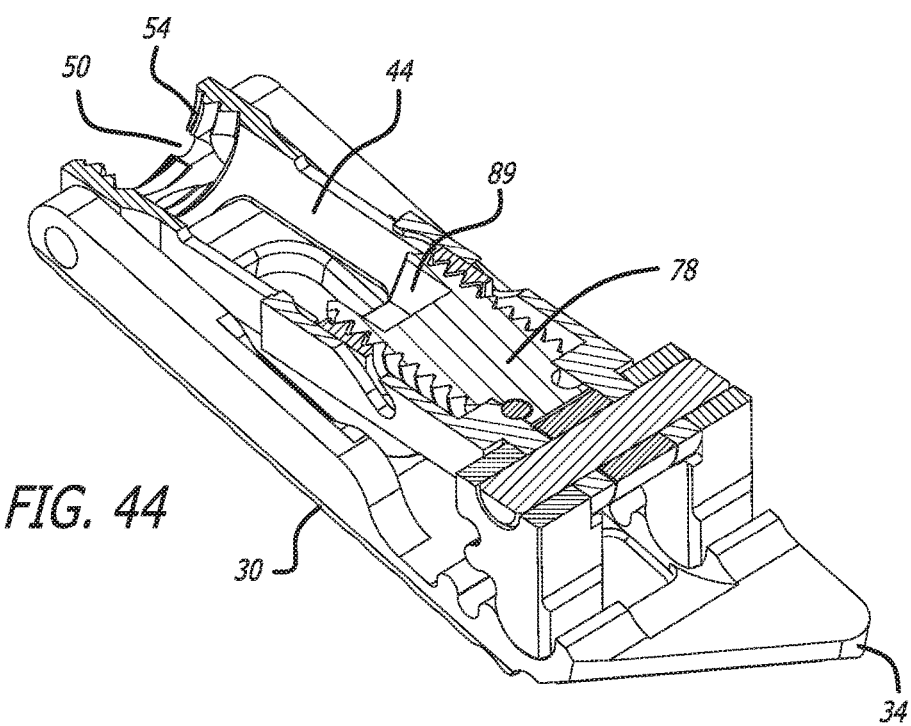
FIG. 44 is an upper perspective cross sectional view of a geared cam expandable implant inserted into the disc space, following removal of the implant insertion tool.

In one embodiment, as depicted in FIGS. 38, 39, and 42, moving the elongated driver 143, either by applying a force to the T-handle 158, or by applying a force to the tap cap 144, the elongated driver 143 is moved through the inner shaft 138, through the opening 50 in the proximal end 46 of the chassis portion 44, and through the chassis portion 44, until the blunt proximal end opening 89 in the rotating portion 78. Translation of the motion of the elongated driver 143 to the rotating portion 78 pushes the implant 10 into the disc space. Following removal of the elongated driver 143 from the implant 10 and the inner shaft 138, as depicted in FIG. 44, bone growth material can be inserted through the inner shaft 138 and into the implant 10.

In one embodiment, as depicted in FIGS. 50-54, upper spikes 174 and lower spikes 176 are pivotally connected to the walls 62 and 64 of the yoke 60. Each upper spike 174 includes a proximal end 177 pivotally connected to a wall of the yoke, and a distal end 178. Each lower spike 176 includes a proximal end 180 pivotally connected to a wall of the yoke, and a distal end 182. Each distal end 178 includes an upper arcuate distal end portion 184 and an upper edge 185. Each distal end 182 includes a lower arcuate distal end portion 186 and a lower distal edge 188.

Figure 52:
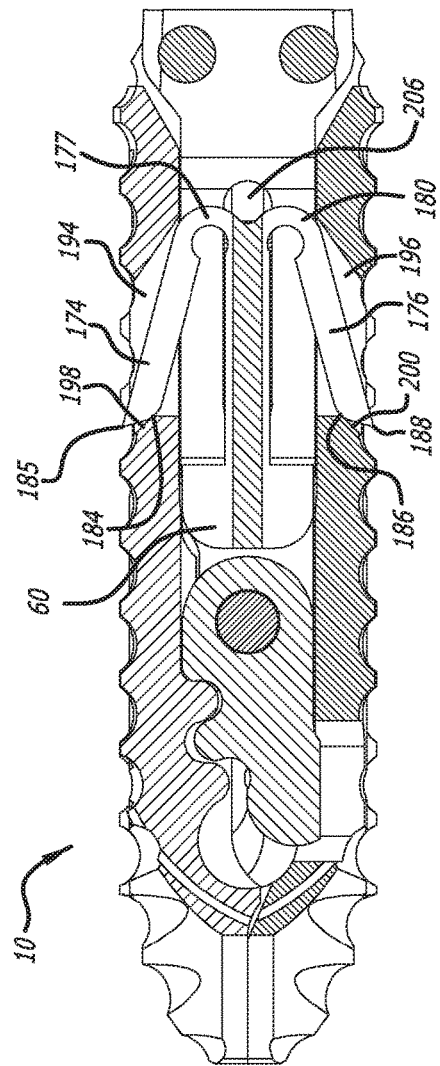
FIG. 52 is a side view of a geared cam expandable implant in accordance with the invention, including deployable spikes, pivotally attached to the implant, in a collapsed position.

In one embodiment, as depicted in FIG. 52, upper pockets 190 are defined within the implant 10 to store the upper spikes 174 when the implant 10 is in the collapsed position. Likewise, lower pockets 192 are defined within the implant 10 to store the lower spikes 176 when the implant 10 is in the collapsed position.

Figure 50:
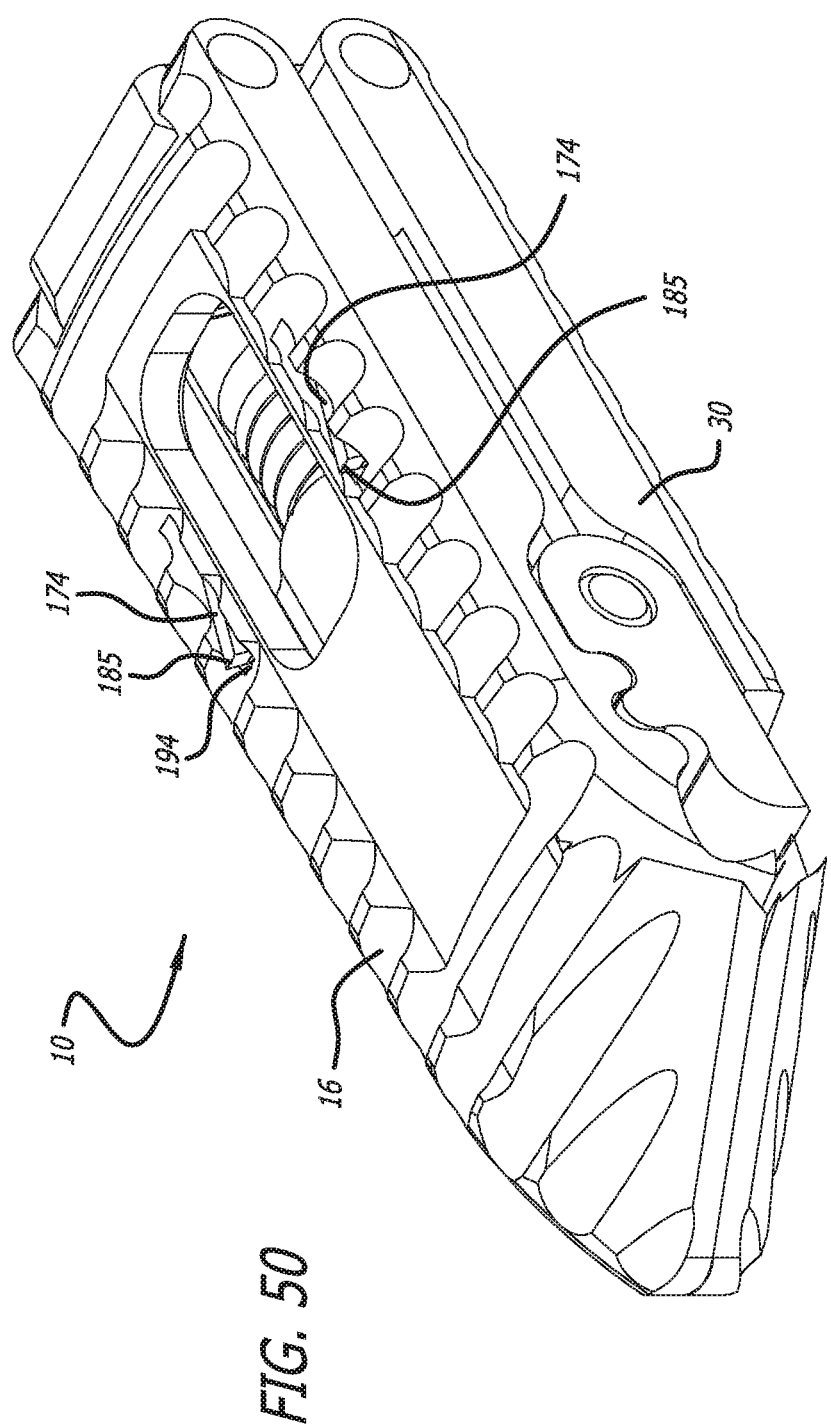
FIG. 50 is a perspective view of a geared cam expandable implant in accordance with the invention, including deployable spikes, pivotally attached to the implant, in a fully-expanded position.
Figure 51:
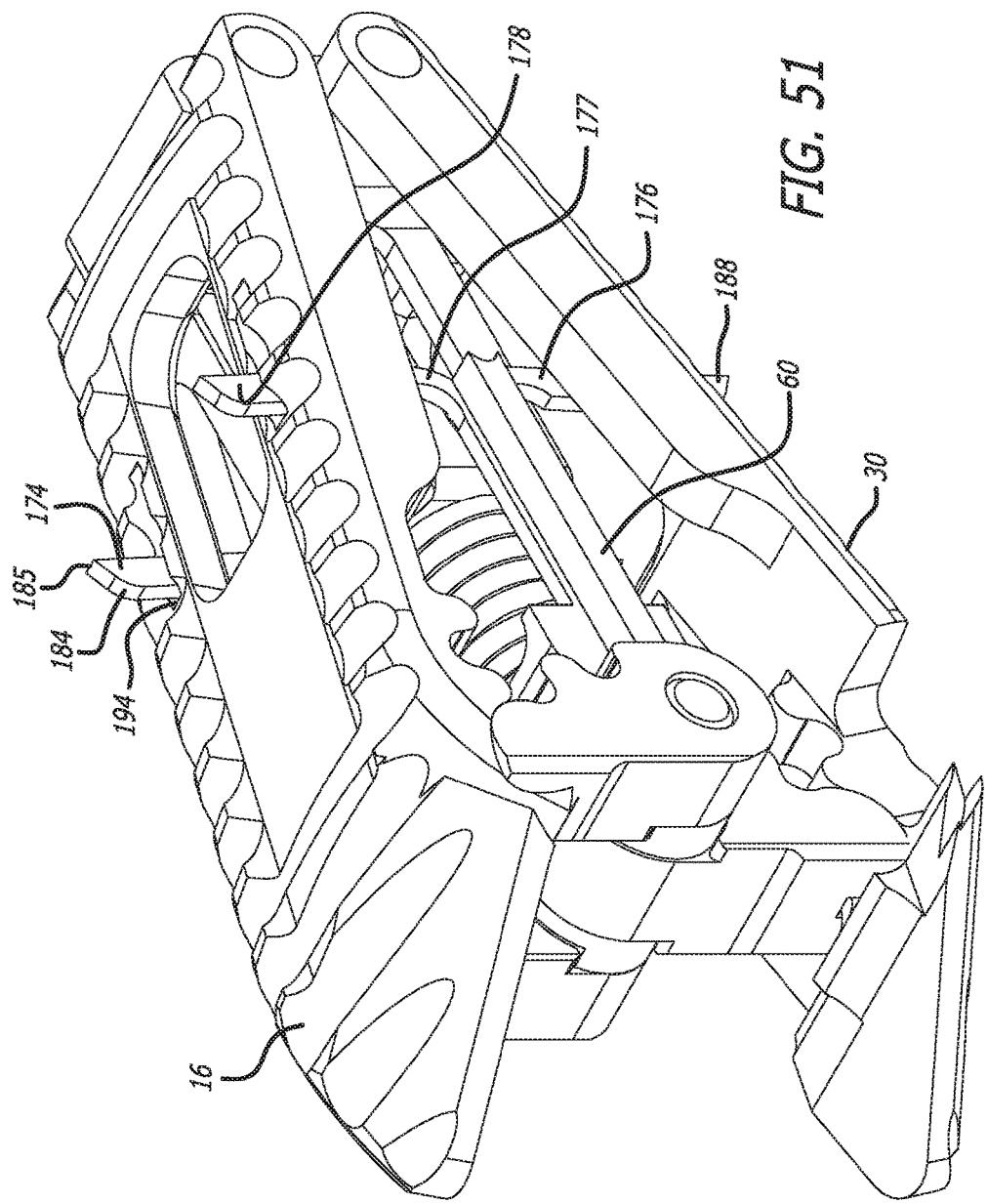
FIG. 51 is a perspective view depicting a chassis portion, a yoke, a rotating portion, spur gears, and deployable spikes pivotally attached to the yoke, of a geared cam expandable implant in accordance with the invention.
Figure 53:
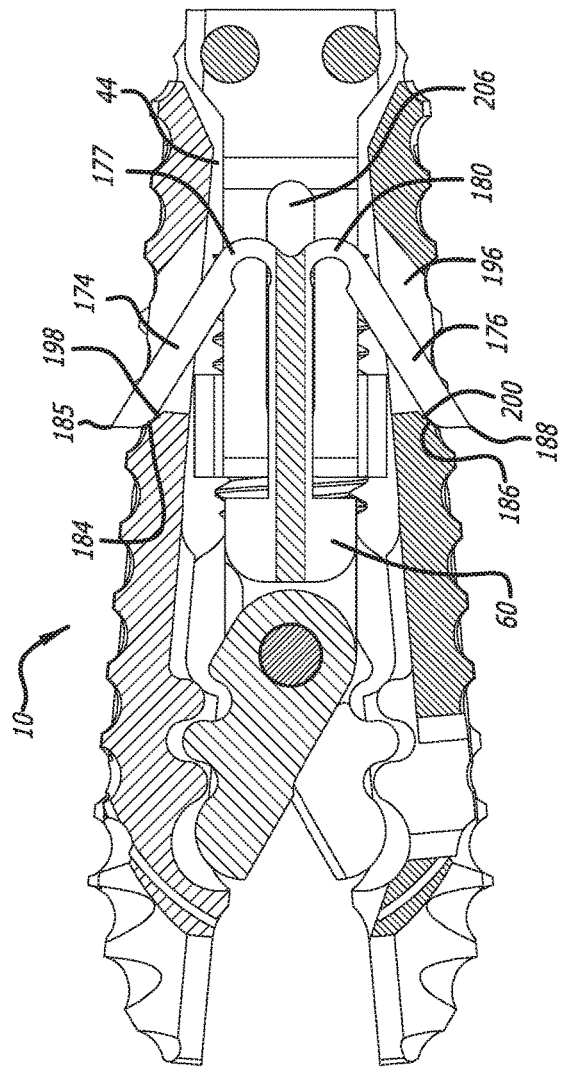
FIG. 53 is a side view of a geared cam expandable implant in accordance with the invention, including deployable spikes, pivotally attached to the implant in a partially expanded position.
Figure 54:
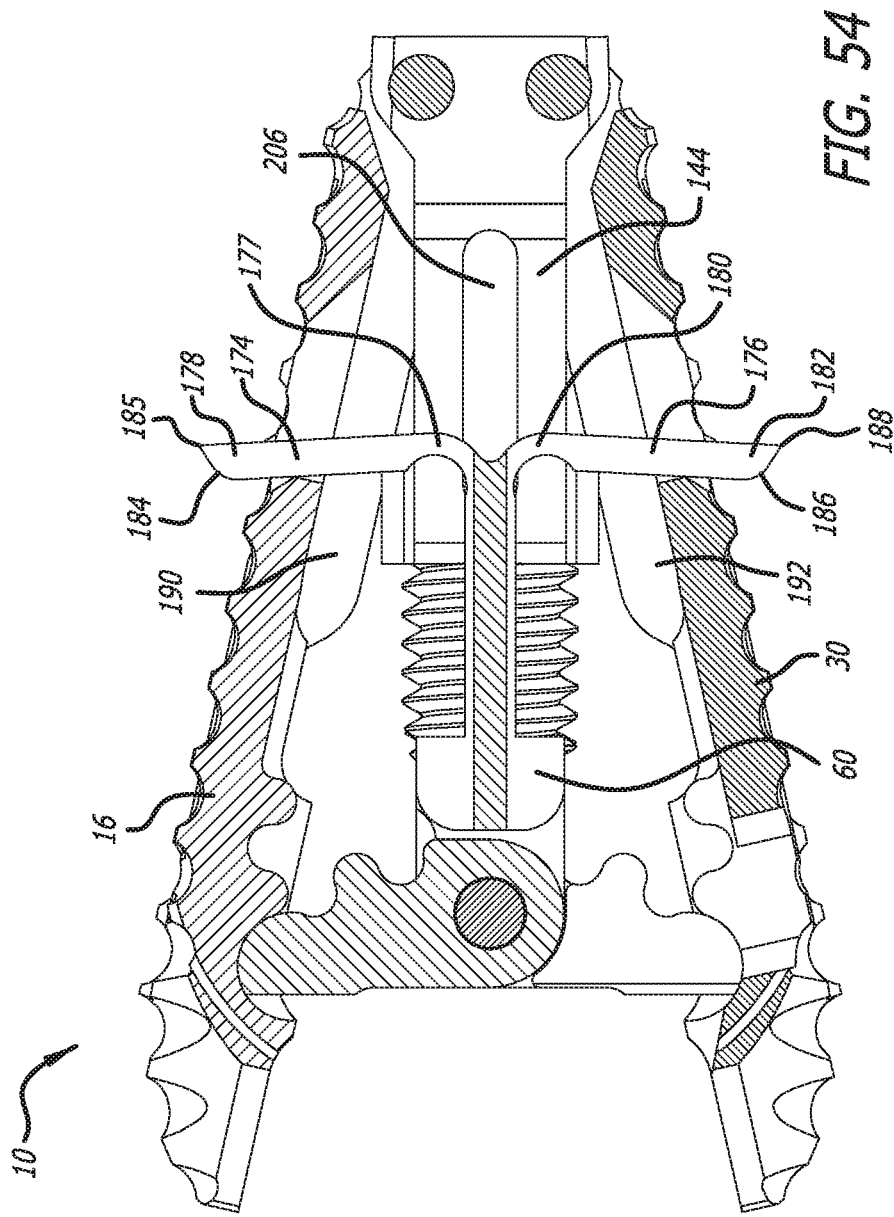
FIG. 54 is a side view of a geared cam expandable implant in accordance with the invention, including deployable spikes, pivotally attached to the implant, in a fully expanded position.

In one embodiment, as depicted in FIGS. 50, 52 and 53, an upper opening 194 is defined in the upper endplate 16 proximate the upper pocket 190. A lower opening 196 is defined in the lower endplate 30 proximate the lower pocket 192. The upper opening 194 includes an upper ramped surface 198 at a distal end thereof, and the lower opening 196 includes a lower ramped surface 200 at a distal end thereof. When the yoke 60 begins to move in the distal direction, and the implant 10 begins to expand, the upper spikes 174 and the lower spikes 176 are simultaneously pushed by the yoke 60 in the distal direction. Upper arcuate distal end portions 184 of the upper spikes 174 are pushed into contact with the upper ramped surface 198 of the upper opening 194 in the upper endplate 16, and lower arcuate distal end portions 186 of the lower spikes 176 are pushed into contact with the lower ramped surface 200 of the lower opening 196 of the lower endplate 30. The distal force applied by the yoke 60, pushing the upper arcuate distal end portions 184 of the upper spikes 174 into contact with the upper ramped surface 198 defined in the distal end of the upper opening 194 defines a torque T (upper). Torque T (upper) forces the upper spikes 174 to pivot clockwise, through the upper opening 194. Likewise, the distal force applied by the yoke 60, pushing the arcuate distal end portions 186 of the lower spikes 176 into contact with the lower ramped surface 200 of the lower opening 196 defines a torque T (lower). Torque T (lower) forces the lower spikes 176 to pivot counter-clockwise, through the lower opening 196 in the lower endplate 30. As the implant 10 continues to expand, the upper spikes 174 continue to pivot until they reach an orientation along an axis which is transverse to the mid-longitudinal axis L-L of the implant 10, with the upper edges 185 engaging the upper vertebral body. Likewise, the lower spikes 176 continue to pivot until they reach an orientation along an axis transverse to the mid-longitudinal axis L-L of the implant 10, with the lower edges 188 engaging the lower vertebral body.

Figure 55:
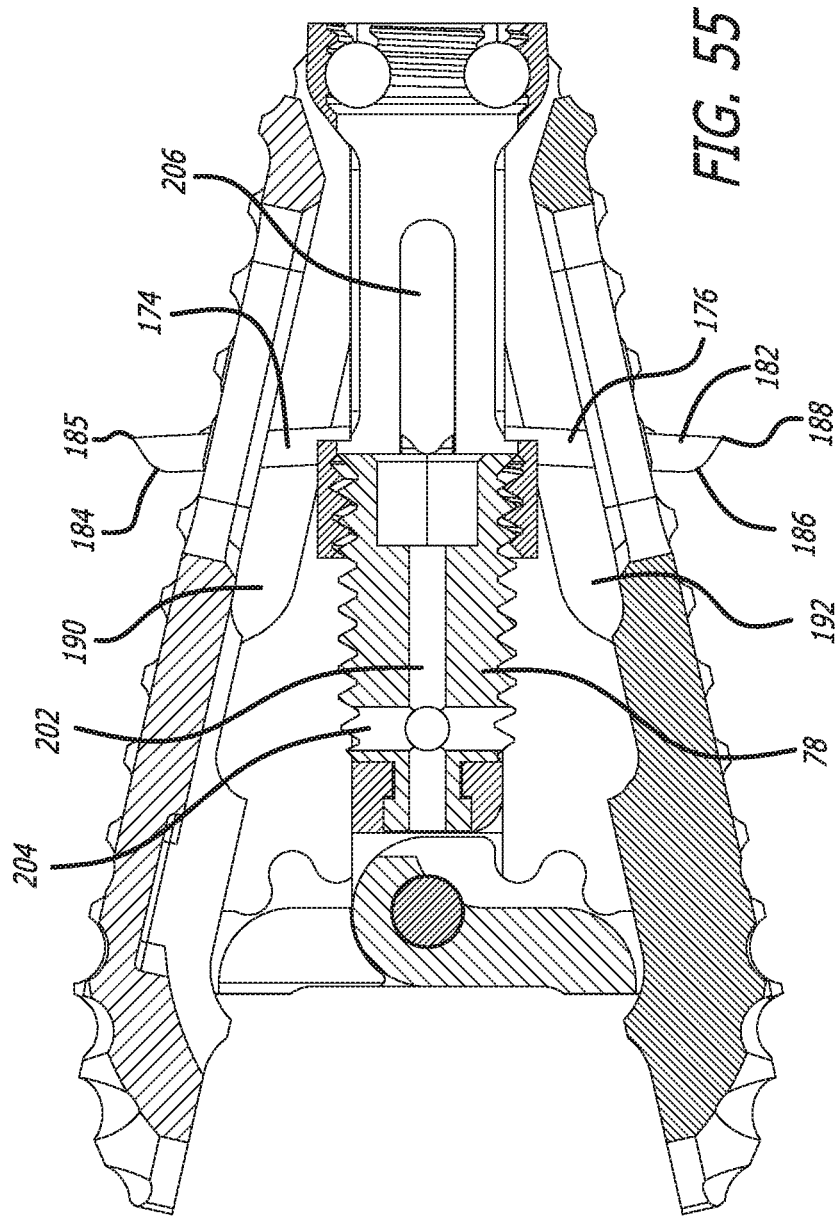
FIG. 55 is a side view of a geared cam expandable implant in accordance with the invention, including deployable spikes, pivotally attached to the implant, and including apertures defined through internal parts, in a fully expanded position.
Figure 56:
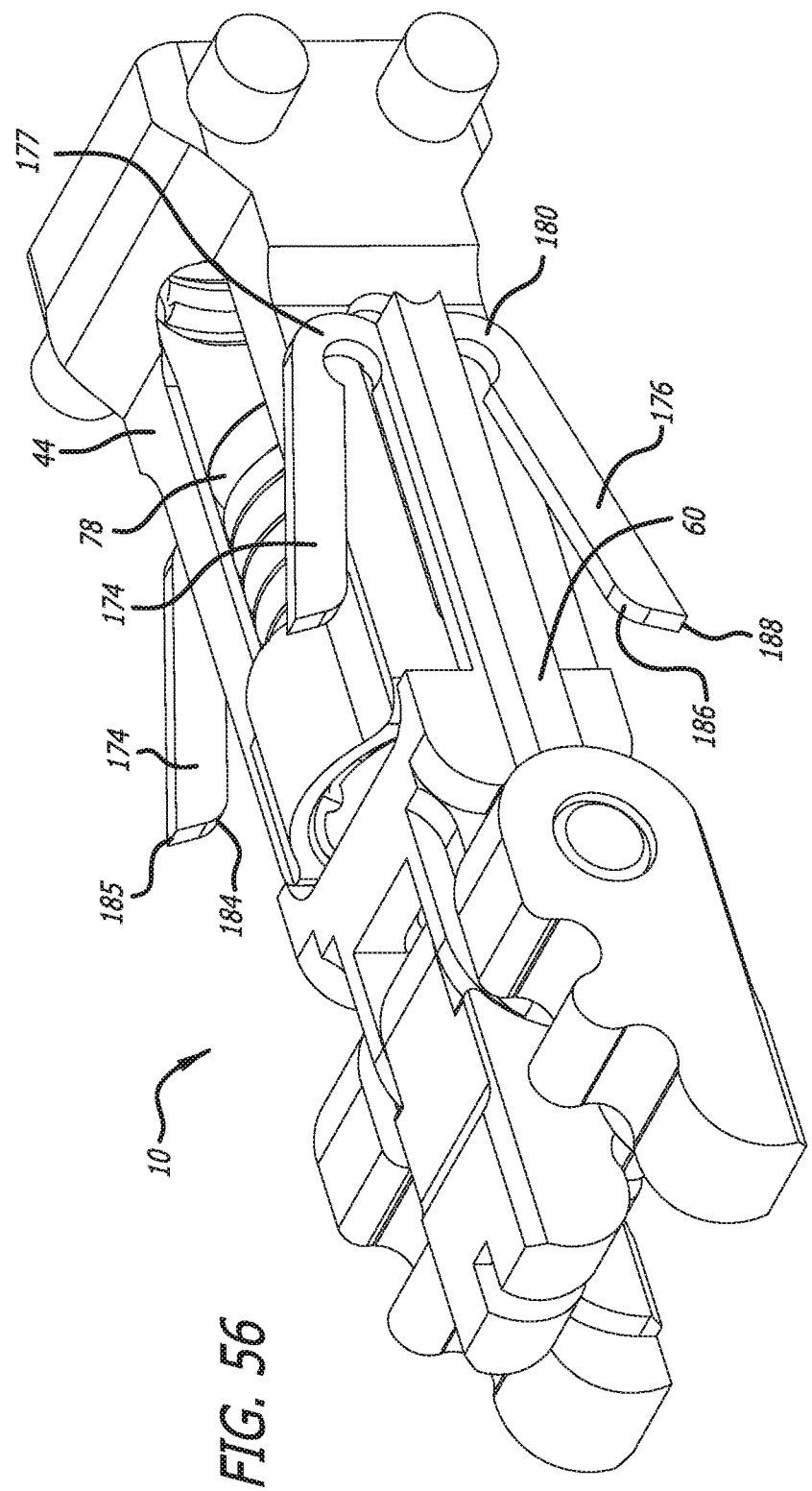
FIG. 56 is a side view of a geared cam expandable implant in accordance with the invention, in a collapsed position, including deployable spikes, pivotally attached to the implant, and including lateral openings to allow flow of bone graft material out of sides of the implant, and further including a planar portion in the upper endplate to distribute load forces, in a fully expanded position.

In one embodiment, as depicted in FIG. 55, apertures can be defined in internal parts of the implant, for example co-axial apertures 202 and transverse apertures 204 defined in the rotating portion 78. The apertures 202 and 204 are configured to permit flow of bone graft material therethrough as it is injected from the proximal end 46 of the chassis 44.

In one embodiment, as depicted in FIG. 55, as the yoke 60 moves in the distal direction, deploying the upper and lower spikes 174 and 176, a co-axial aperture 206 is opened in the chassis 44 behind the proximal ends 177 and 180 of the spikes 174 and 176, respectively. Co-axial aperture 206 also is configured to allow a flow of bone growth material therethrough.

In one embodiment, as depicted in FIG. 57, flaps 208 are attached to the right and left sides of the implant 10 (only one side shown), with upper and lower edges thereof connected between the upper endplate 16 and the lower endplate 30. The flaps 208 can be made of a porous material, a semi-porous material, or a solid material. When the implant 10 is expanded, as depicted in FIG. 57, the flaps 208 are deployed, stretched tightly between the upper endplate 16 and the lower endplate 30.

Figure 62:
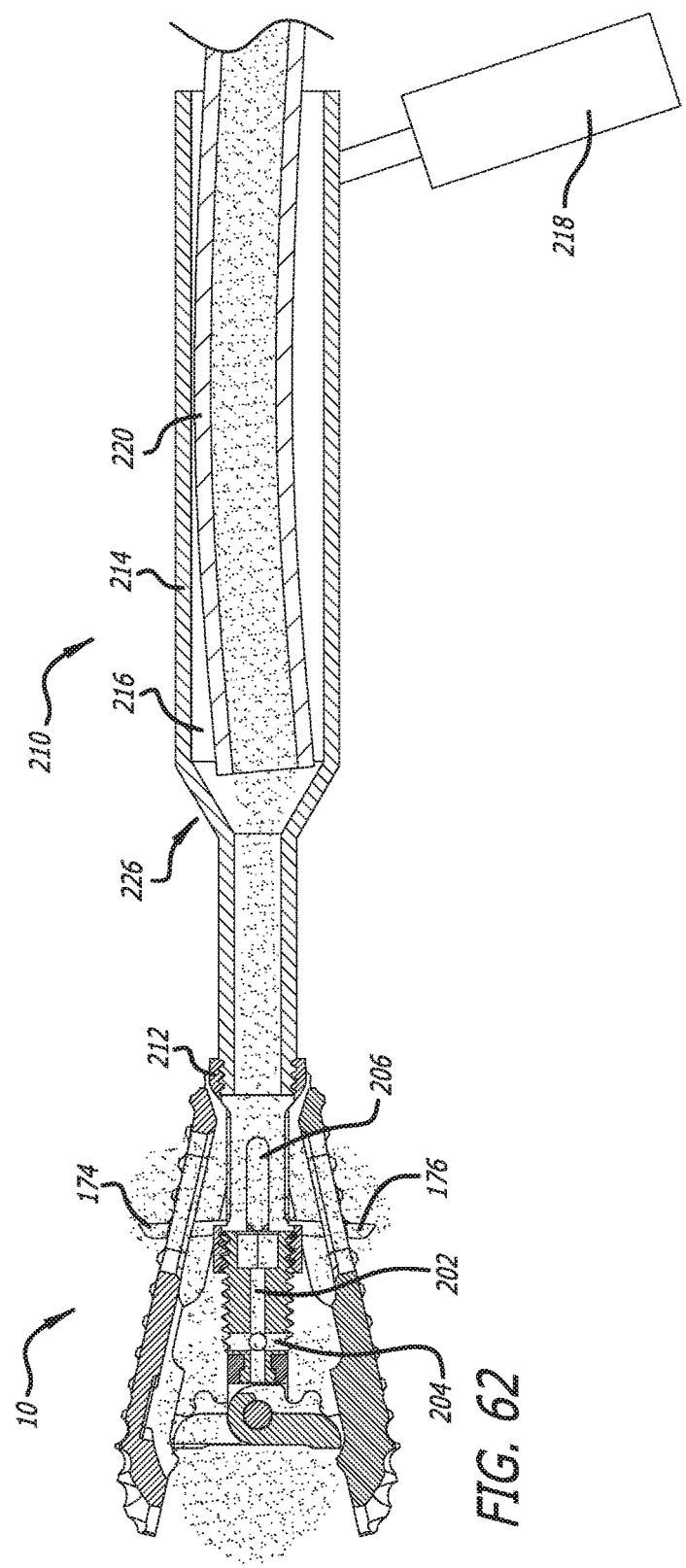
FIG. 62 is a side cross-sectional view of a geared cam expandable implant in accordance with the invention, in a fully expanded position, with a bone graft insertion apparatus connected to a proximal end of the implant, and a graft insertion tube filled with bone graft material provided within the bone graft insertion apparatus.

In one embodiment, as depicted in FIGS. 60-62, an implant 10 includes a bone graft inserter 210, attachable to attachment clamps 212 provided at the proximal end 46 of the chassis portion 44. The bone graft inserter includes an outer tube 214 defining a lumen 216 therethrough, and a handle 218. The attachment clamps 212 are positioned to firmly grip a distal end of the outer tube 214.

In one embodiment, as depicted in FIGS. 60-62, a graft tube 220 is provided within the lumen 216. Bone graft material in the graft tube 220 is in position to flow into the chassis portion 44 of the implant 10 via the connection between the attachment clamps 212 and the outer tube 214. As further depicted in FIGS. 60-62, the bone graft material inserted into the chassis portion 44 of the implant 10 can flow out of the implant 10 via multiple small apertures (not shown) in the upper and lower endplates 16 and 30, respectively, and via the open distal end of the expanded implant 10.

In one embodiment, as depicted in FIGS. 58 and 59, a rigid plunger 222 is provided in the lumen 216. The plunger 222 includes a head portion 224 at a distal end thereof. The head portion 224 has a diameter approximately equal to a diameter of the lumen 216. When the plunger 222 slides within the lumen 216 in the distal direction, the head portion 224 pushes bone graft material in the distal direction and into the proximal end 46 of the chassis portion 44.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. An expandable spinal implant comprising:
   a proximal end and a distal end defining a mid-longitudinal axis therebetween the expandable spinal implant being configured for insertion into a patient's disc space between an upper vertebral body and a lower vertebral body, and the expandable spinal implant being expandable between a collapsed position, a fully expanded position, and at least one partially expanded position between the collapsed position and the fully expanded position;
   an upper endplate, the upper endplate including a proximal end, a distal end, an outer surface, at least one side surface, and an inner surface, a portion of the inner surface including an upper rack portion, the upper rack portion including at least one downwardly-projecting tooth intermediate the proximal end and the distal end of the upper endplate, and at least one distal-most downwardly-projecting tooth proximate the distal end of the upper endplate;
   a lower endplate, the lower endplate including a proximal end, a distal end, an outer surface, at least one side surface, and an inner surface, a portion of the inner surface including a lower rack portion, the lower rack portion including at least one upwardly-projecting tooth intermediate the proximal end and the distal end of the lower endplate, and at least one distal-most upwardly-projecting tooth proximate the distal end of the lower endplate, the proximal end of the lower endplate being pivotally connected to the proximal end of the upper endplate;
   a chassis portion mounted within the implant between the upper endplate and the lower endplate, the chassis portion having a proximal end and a distal end, the proximal end having an opening defined therein, at least one depression defined therein proximate the opening, a first set of inner threads defined in the opening, and a second set of inner threads defined intermediate the proximal end and the distal end of the chassis portion;
   a yoke movably mounted with respect to the chassis portion, the yoke having a proximal end and a distal end, and being defined by first and second substantially parallel spaced apart walls, each of the first and second spaced apart walls having a proximal end and a distal end;
   a rotating portion rotatably mounted within the chassis portion, the rotating portion having an outer surface, a proximal end and a distal end, the proximal end having an opening defined therein, the distal end being positioned proximate the distal end of the yoke, and threads defined on at least a portion of the outer surface, the threads being engageable with the second set of inner threads in the chassis portion;
   at least one first spur gear rotatably mounted to at least one of the distal ends of at least one of the first and second spaced apart walls of the yoke, the at least one first spur gear having at least one projecting first spur gear tooth configured to movably engage with the downwardly-depending teeth on the upper rack portion;
   at least one second spur gear rotatably mounted to at least one of the distal ends of at least one of the first and second spaced apart walls of the yoke, the at least one second spur gear having at least one projecting second spur gear tooth configured to engage with the upwardly-projecting teeth on the lower rack portion; and
   at least one spike pivotally attached to at least one of the first and second spaced apart walls of the yoke;
   wherein the rotating portion is further configured to translate rotational motion thereof to linear motion of the yoke, the yoke translating the linear motion to rotational motion of at least the at least one first spur gear, thereby rotating the at least one first spur gear with respect to the yoke;
   wherein the rotation of the at least one first spur gear with respect to the yoke defines a first linear walking motion of the at least one projecting first spur gear tooth along the downwardly-depending upper rack gear teeth toward the distal end of the implant, thereby pivoting the upper endplate to the at least one partially expanded position; and
   wherein the linear motion of the yoke is translated to pivotal motion of the at least one spike from a collapsed position, to a fully deployed position transverse to the mid-longitudinal axis.

2. The expandable spinal implant of claim 1, wherein at least one of the upper endplate and the lower endplate includes at least one projection projecting from the outer surface thereof, the at least one projection configured to engage a corresponding endplate of a respective one of the upper vertebral body and the lower vertebral body.

3. The expandable spinal implant of claim 1, wherein the yoke further includes at least one side surface, the at least one side surface having a track defined therein, the track being configured to receive therein a peg projecting from the at least one side surface of one of the lower endplate and the upper endplate, thereby preventing disengagement of the upper endplate from the lower endplate.

4. The expandable spinal implant of claim 1, wherein the rotation of the rotating portion further translates motion to at least the at least one second spur gear to rotate the at least one second spur gear with respect to the yoke, the rotation of the at least one second spur gear with respect to the yoke defining a second linear walking motion of the at least one projecting second spur gear tooth along the upwardly-projecting lower rack gear teeth toward the distal end of the implant, pivoting the lower endplate to the at least one partially expanded position.

5. The expandable spinal implant of claim 4, wherein at least the lower rack portion includes a distal-most upwardly-projecting lower rack gear tooth being configured to interact with the at least one second spur to stop the second linear walking motion.

6. The expandable spinal implant of claim 1, further comprising at least one pocket defined between the upper endplate and the lower endplate configured to house the at least one spike when the implant is in the collapsed position.

7. The expandable spinal implant of claim 1, wherein the pivotal motion of the at least one spike to the fully deployed position exposes at least one window defined in at least the chassis portion.

8. The expandable spinal implant of claim 7, wherein the at least one window defined in at least the chassis portion is configured to allow flow of bone graft material therethrough.

9. The expandable spinal implant of claim 1, wherein the rotating portion is generally cylindrical.

10. The expandable spinal implant of claim 9, wherein the rotating portion includes at least one aperture defined in the outer peripheral surface, the at least one aperture being configured to allow flow of bone graft material therethrough.

11. The expandable spinal implant of claim 1, wherein the at least one spike pivotally attached to the one of the first and second spaced apart walls of the yoke further comprises at least two spikes pivotally attached to the one of the first and second spaced apart walls of the yoke.

12. The expandable implant of claim 1, wherein the at least one spike pivotally attached to the one of the first and second spaced apart walls of the yoke further comprises a first pair of spikes pivotally attached to the first wall of the yoke, and a second pair of spikes pivotally attached to the second wall of the yoke.

13. The expandable spinal implant of claim 1, wherein at least the upper rack portion includes a distal-most downwardly-depending upper rack gear tooth being configured to interact with the at least one first spur gear to stop the first linear walking motion.

14. The expandable spinal implant of claim 1, further comprising at least one opening defined in at least one of the upper endplate and the lower endplate, the at least one opening being configured for the at least one spike to pass therethrough when the at least one spike pivots to the fully deployed position.

15. The expandable spinal implant of claim 14, wherein the at least one opening includes a proximal end, a distal end, and a ramped portion defined at the distal end, the ramped portion being positioned to contact an arcuate portion defined on a distal end of the at least one spike, wherein contact between the ramped portion and the arcuate portion defines a torque, the torque pivoting the at least one spike to the fully deployed position.

16. The expandable spinal implant of claim 1, wherein a distal edge portion of the at least one spike, in the fully deployed position, is configured to contact at least one of the upper vertebral body and the lower vertebral body and prevent inadvertent backout of the implant from the disc space.

17. A kit for inserting an expandable spinal implant into a patient's disc space between an upper vertebral body and a lower vertebral body, the kit comprising:
the implant, the implant comprising:
a proximal end and a distal end defining a mid-longitudinal axis therebetween, the expandable spinal implant being expandable between a collapsed position, a fully expanded position, and at least one partially expanded position between the collapsed position and the fully expanded position;
an upper endplate, the upper endplate including a proximal end, a distal end, an outer surface, at least one side surface, and an inner surface, a portion of the inner surface including an upper rack portion, the upper rack portion including at least one downwardly-projecting tooth intermediate the proximal end and the distal end of the upper endplate, and at least one distal-most downwardly-projecting tooth proximate the distal end of the upper endplate;
a lower endplate, the lower endplate including a proximal end, a distal end, an outer surface, at least one side surface, and an inner surface, a portion of the inner surface including a lower rack portion, the lower rack portion including at least one upwardly-projecting tooth intermediate the proximal end and the distal end of the lower endplate, and at least one distal-most upwardly-projecting tooth proximate the distal end of the lower endplate, the proximal end of the lower endplate being pivotally connected to the proximal end of the upper endplate;
a chassis portion mounted within the implant between the upper endplate and the lower endplate, the chassis portion having a proximal end and a distal end, the proximal end having an opening defined therein, at least one depression defined therein proximate the opening, a first set of inner threads defined in the opening, and a second set of inner threads defined intermediate the proximal end and the distal end of the chassis portion;
a yoke movably mounted with respect to the chassis portion, the yoke having a proximal end and a distal end, and being defined by first and second substantially parallel spaced apart walls, each of the first and second spaced apart walls having a proximal end and a distal end;
a rotating portion rotatably mounted within the chassis portion, the rotating portion having an outer surface, a proximal end, and a distal end, the proximal end having an opening defined therein, the distal end being positioned proximate the distal end of the yoke, and threads defined on at least a portion of the outer surface, the threads being engageable with the second set of inner threads in the chassis portion;
at least one first spur gear rotatably mounted to at least one of the distal ends of at least one of the first and second spaced apart walls of the yoke, the at least one first spur gear having at least one projecting first spur gear tooth configured to movably engage with the downwardly-depending teeth on the upper rack portion;

at least one second spur gear rotatably mounted to at least one of the distal ends of at least one of the first and second spaced apart walls of the yoke, the at least one second spur gear having at least one projecting second spur gear tooth configured to engage with the upwardly-projecting teeth on the lower rack portion; and at least one spike pivotally attached to one of the first and second spaced apart walls of the yoke;

wherein the rotating portion is further configured to translate rotational motion thereof to linear motion of the yoke, the yoke translating the linear motion to rotational motion of at least the at least one first spur gear, thereby rotating the at least one first spur gear with respect to the yoke;

wherein the rotation of at least the at least one first spur gear with respect to the yoke defines a first linear walking motion of the at least one projecting first spur gear tooth along the downwardly-depending upper rack gear teeth toward the distal end of the implant, thereby pivoting the upper endplate to the at least one partially expanded position; and wherein the linear motion of the yoke translates to pivotal motion of the at least one spike, from a collapsed position to a fully deployed position transverse to the mid-longitudinal axis; and an insertion tool attachable to the proximal end of the implant.

* * * * *

UNITED STATES PATENT AND TRADEMARK OFFICE
CERTIFICATE OF CORRECTION

PATENT NO. : 10,137,007 B2
APPLICATION NO. : 15/147668
DATED : November 27, 2018
INVENTOR(S) : Dewey et al.

Page 1 of 1

It is certified that error appears in the above-identified patent and that said Letters Patent is hereby corrected as shown below:

On the Title Page

In Item (71), under "Applicant", in Column 1, Line 1, delete "Warsaw Orthopedic, Inc," and insert -- Warsaw Orthopedic, Inc., --, therefor.

In the Specification

In Column 5, Line 7, delete "invention." and insert -- invention; --, therefor.

In the Claims

In Column 11, Line 45, in Claim 1, delete "therebetween" and insert -- therebetween, --, therefor.

In Column 13, Line 46, in Claim 12, delete "expandable implant" and insert -- expandable spinal implant --, therefor.

Signed and Sealed this
Sixteenth Day of July, 2019

Andrei Iancu
*Director of the United States Patent and Trademark Office*